(12) United States Patent
Gonzalez Lopez de Turiso et al.

(10) Patent No.: US 11,814,362 B2
(45) Date of Patent: Nov. 14, 2023

(54) ASK1 INHIBITING AGENTS

(71) Applicant: BIOGEN MA INC., Cambridge, MA (US)

(72) Inventors: Felix Gonzalez Lopez de Turiso, Cambridge, MA (US); Michael Dechantsreiter, Allston, MA (US); Zhili Xin, Lexington, MA (US); John H. Jones, Framingham, MA (US); Martin Himmelbauer, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 232 days.

(21) Appl. No.: 17/253,269

(22) PCT Filed: Jun. 26, 2019

(86) PCT No.: PCT/US2019/039156
§ 371 (c)(1),
(2) Date: Dec. 17, 2020

(87) PCT Pub. No.: WO2020/006031
PCT Pub. Date: Jan. 2, 2020

(65) Prior Publication Data
US 2021/0115020 A1    Apr. 22, 2021

Related U.S. Application Data

(60) Provisional application No. 62/690,674, filed on Jun. 27, 2018.

(51) Int. Cl.
*C07D 401/14* (2006.01)
(52) U.S. Cl.
CPC ................ *C07D 401/14* (2013.01)
(58) Field of Classification Search
CPC .................................................. C07D 401/14
See application file for complete search history.

(56) References Cited

U.S. PATENT DOCUMENTS

2011/0009410 A1    1/2011  Corkey et al.

FOREIGN PATENT DOCUMENTS

WO    2018/151830 A1    8/2018

OTHER PUBLICATIONS

Lovering et al., Rational approach to highly potent and selective apoptosis signal-regulating kinase 1 (ASK1) inhibitors. Eur J Med Chem. Dec. 15, 2017; 145:606-621.
International Search Report and Written Opinion for Application No. PCT/US2019/039156, dated Aug. 29, 2019, 10 pages.

*Primary Examiner* — Brian E McDowell
(74) *Attorney, Agent, or Firm* — McCarter & English, LLP; Steven G. Davis; Xin Zhang

(57) ABSTRACT

Provided are compounds of Formula (I): including compounds of Formulas (II), (III) and (IV), wherein X, $R^1$, $R^2$, $R^3$ and n are as defined herein, and pharmaceutically acceptable salts thereof, and methods for their use and production. These compounds can be useful, e.g., in the treatment of disorders responsive to the inhibition of apoptosis signal-regulating kinase 1 (ASK1).

(I)

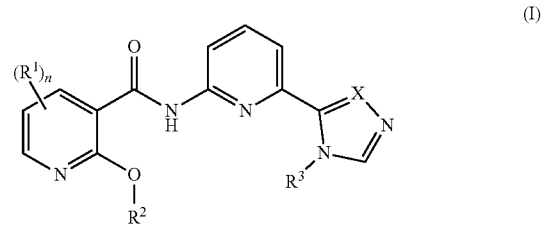

16 Claims, No Drawings

ASK1 INHIBITING AGENTS

CROSS REFERENCE TO RELATED APPLICATIONS

This application is a 35 U.S.C. § 371 national stage filing of International Application No. PCT/US2019/039156, filed on Jun. 26, 2019, which in turn claims priority to U.S. Provisional Patent Application No. 62/690,674, filed Jun. 27, 2018; the contents of each of which are incorporated herein by reference in their entirety.

TECHNICAL FIELD

Provided are certain agents that inhibit apoptosis signal-regulating kinase 1 (ASK1), and methods of making and using such agents.

BACKGROUND

Apoptosis Signal-regulating Kinase 1 (ASK1), also known as MAP3K5, is a member of the mitogen-activated protein kinase kinase kinase ("MAP3K") family that activates the c-Jun N-terminal protein kinase ("JNK") and p38 MAP kinase (Ichijo, H. et al., Science 1997, 275, 90-94). ASK1 is an evolutionary conserved and stress-responsive mitogen-activated protein kinase (MAPK). In mouse, ASK1 has been found to be expressed in heart, brain, lung, liver and kidney, as well as in developing skin, cartilage and bone (Tobiume et al., Biochem Biophys Res Commun. 1997, 239(3), 905-10). ASK1 is a central regulator of cell death and participates in several stress-induced and receptor-mediated cell death pathways triggered by various forms of cellular stress, including oxidative stress, reactive oxygen species (ROS), endoplasmic reticulum (ER) stress and unfolded protein response (UPR), mitochondrial stress, bacterial infection, increased calcium influx, DNA damage, UV radiation, viral infection, heat shock, osmotic shock, endotoxic lipopolysaccharide (LPS), FasL, and activation by pro-inflammatory cytokines such as tumor necrosis factor (TNF) and interleukin-1 (Nishitoh et al., Genes Dev. 2002, 16, 1345-1355; Matsukawa et al., Nat. Immunol., 2005, 6, 587-592; Tobiume et al., EMBO Rep. 2001, 2, 222-228; Hayakawa R. et al., Proc. Jpn. Acad. Ser B Phys. Biol. Sci. 2012, 88(8), 434-53; Takeda et al. Cell Struct. Funct. 2003, 28(1), 23-29; Tibbles et al., Cell Mol Life Sci. 1999, 55(10), 1230-1254; Hattori et al., Cell Comm. Signal. 2009, 7, 1-10; Takeda et al., Annu. Rev. Pharmacol. Toxicol. 2007, 48, 1-8.27; Nagai et al. J. Biochem. Mol. Biol. 2007, 40, 1-6).

ASK1 undergoes activation via autophosphorylation at Thr838 in response to these signals and in turn phosphorylates MAP2Ks, such as MKK3/6 and MKK4/7, which then phosphorylate and activate p38 and JNK MAPKs, respectively. Activation of the JNK and p38 pathways induces stress responses related to cell death, differentiation and the production of inflammatory cytokines. In non-stressed conditions, ASK1 is kept in an inactive state through binding to its repressor Thioredoxin (Trx) (Saitoh, M. et al., Embo J. 1998, 17, 2596-2606), and through association with AKT (Zhang, L., et al. Proc. Natl. Acad. Sci. U.S.A 1999, 96, 8511-8515).

ASK1 plays an essential role not only in cell death pathways, but also in inflammatory and innate immune responses including cytokine responses, and cell differentiation. Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. BBRC 2005, 333, 562-567; Zhang et al., Life Sci 2003, 74-37-43; Terada et al. BBRC 2007, 364: 1043-49).

Therefore, there is a need for new compounds that can function as ASK1 inhibitors.

SUMMARY

A first embodiment of the invention is a compound of Formula (I):

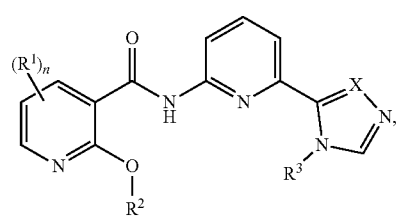

(I)

or a pharmaceutically acceptable salt thereof, wherein:

X is $CR^4$ or N;

n is 1 or 2;

$R^1$ in each occurrence is independently selected from H, $C_{1-6}$alkyl, $C_{2-6}$alkenyl, $C_{2-6}$alkynyl, halo, —CN, —C(O)$R^{1a}$, —C(O)O$R^{1a}$, —C(O)N($R^{1a}$)$_2$, —N($R^{1a}$)$_2$, —N($R^{1a}$)C(O)$R^{1a}$, —N($R^{1a}$)C(O)O$R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, and $C_{2-6}$alkynyl are optionally substituted with one or more $R^{10}$;

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally and independently substituted with one or more $R^{20}$;

$R^{20}$ in each occurrence is independently selected from $C_{1-6}$alkyl, halo and —$OR^{20a}$;

$R^{20a}$ is H or $C_{1-4}$alkyl;

$R^3$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally substituted with one or more $R^{30}$;

$R^{30}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, carbocyclyl, and heterocyclyl, wherein said carbocyclyl, and heterocyclyl are each optionally substituted with one or more substituents independently selected from $C_{1-4}$alkyl and halo;

$R^4$ is selected from H, $C_{1-6}$alkyl, $C_{2-6}$alkenyl, $C_{2-6}$alkynyl, carbocyclyl, heterocyclyl, halo, —CN, —C(O)$R^{4a}$, —C(O)O$R^{4a}$, —C(O)N($R^{4a}$)$_2$, —N($R^{4a}$)$_2$, —N($R^{4a}$)C(O)$R^{4a}$, —N($R^{4a}$)C(O)O$R^{4a}$, —N($R^{4a}$)C(O)N($R^{4a}$)$_2$, —N($R^{4a}$)S(O)$_2$$R^{4a}$, —O$R^{4a}$, —OC(O)$R^{4a}$, —OC(O)N($R^{4a}$)$_2$, —S$R^{4a}$, —S(O)$R^{4a}$, —S(O)$_2$$R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, carbocyclyl, and heterocyclyl, are optionally substituted with one or more $R^{40}$;

$R^{40}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{40a}$, —C(O)O$R^{40a}$, —C(O)N($R^{40a}$)$_2$, —N($R^{40a}$)$_2$, —N($R^{40a}$)C(O)$R^{40a}$, —N($R^{40a}$)C(O)O$R^{40a}$, —N($R^{40a}$)C(O)N($R^{40a}$)$_2$, —N($R^{40a}$)S(O)$_2$$R^{40a}$, —O$R^{40a}$, —OC(O)$R^{40a}$, —OC(O)N($R^{40a}$)$_2$, —S$R^{40a}$, —S(O)$R^{40a}$, —S(O)$_2$$R^{40a}$, —S(O)N($R^{40a}$)$_2$, and —S(O)$_2$N($R^{40a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{40a}$, —C(O)O$R^{40a}$, —C(O)N($R^{40a}$)$_2$, —N($R^{40a}$)$_2$, —N($R^{40a}$)C(O)$R^{40a}$, —N($R^{40a}$)C(O)O$R^{40a}$, —N($R^{40a}$)C(O)N($R^{40a}$)$_2$, —N($R^{40a}$)S(O)$_2$$R^{40a}$, —O$R^{40a}$, —OC(O)$R^{40a}$, —OC(O)N($R^{40a}$)$_2$, —S$R^{40a}$, —S(O)$R^{40a}$, —S(O)$_2$$R^{40a}$, —S(O)N($R^{40a}$)$_2$, and —S(O)$_2$N($R^{40a}$)$_2$; and $R^{40a}$ in each occurrence is independently selected from H and $C_{1-4}$alkyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of ASK1 in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of ASK1. Also provided is a compound described herein, or a pharmaceutically acceptable salt thereof for use in treating a disorder responsive to inhibition of ASK1.

Other features or advantages will be apparent from the following detailed description of several embodiments, and also from the appended claims.

DETAILED DESCRIPTION

The compounds or pharmaceutically acceptable salts thereof as described herein, can have activity as ASK1 modulators. In particular, compounds or pharmaceutically acceptable salts thereof as described herein, can be ASK1 inhibitors.

In a second embodiment of the invention, the compound is represented by Formula (II):

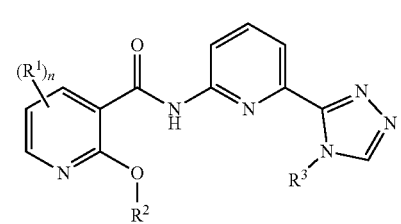

(II)

or a pharmaceutically acceptable salt thereof, wherein $R^1$, $R^2$, $R^3$ and n are as described in the first embodiment.

In a third embodiment, the compound is represented by Formula (I) or (II), or pharmaceutically acceptable salt thereof, wherein $R^2$ is $C_{1-6}$alkyl, and the values of the other variables are as defined in the first or second embodiment.

In a fourth embodiment, the compound is represented by Formula (I) or (II), or a pharmaceutically acceptable salt thereof, wherein $R^2$ is $CH_3$, and the values of the other variables are as defined in the first or second embodiment.

In a fifth embodiment, the compound is represented by Formula (I) or (II), or a pharmaceutically acceptable salt thereof, wherein n is 1, and the values of the other variables are as defined in the first, second, third or fourth embodiment.

In a sixth embodiment, the compound is represented by Formula (III):

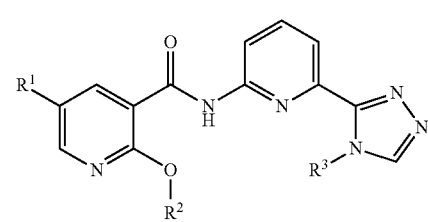

(III)

or a pharmaceutically acceptable salt thereof, wherein variables are as defined in the first, second, third, or fourth embodiment.

In a seventh embodiment, the compound is represented by Formula (I), (II) or (III), or a pharmaceutically acceptable salt thereof, wherein:

$R^1$ in each occurrence is independently selected from H, $C_{1-6}$alkyl, $C_{2-6}$alkenyl, $C_{2-6}$alkynyl, halo, —CN, —C(O)$R^{1a}$, —C(O)O$R^{1a}$, —C(O)N($R^{1a}$)$_2$, —N($R^{1a}$)$_2$, —O$R^{1a}$, —S(O)$_2R^{1a}$, and —S(O)$_2$N($R^{1a}$)$_2$, wherein said $C_{1-6}$alkyl, $C_{2-6}$alkenyl and $C_{2-6}$alkynyl are optionally substituted with one to four $R^{10}$;

$R^{1a}$ in each occurrence is independently selected from H, $C_{1-6}$alkyl, and 4- to 7-membered monocyclic N-containing non-aromatic heterocyclyl, wherein said $C_{1-6}$alkyl, and 4- to 7-membered monocyclic N-containing non-aromatic heterocyclyl in each occurrence are optionally and independently substituted with one or three $R^{10}$; and $R^{10}$ in each occurrence is independently selected from $C_{1-6}$alkyl, halo, —N($R^{10a}$)$_2$, —O$R^{10a}$, —N($R^{10a}$)C(O)$R^{10a}$, —C(O)N($R^{10a}$)$_2$, —S$R^{10a}$, —S(O)$_2R^{10a}$, —S(O)$_2$N($R^{10a}$)$_2$, —CN, $C_{3-6}$cycloalkyl, and 4- to 7-membered monocyclic non-aromatic heterocyclyl, wherein said $C_{1-6}$alkyl, $C_{3-6}$cycloalkyl, and 4- to 7-membered monocyclic non-aromatic heterocyclyl are optionally substituted with one or more halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently H, $C_{1-4}$alkyl, halo$C_{1-4}$alkyl or $C_{3-6}$cycloalkyl, and wherein the values of the other variables are as defined for the first, second, third, fourth, fifth or sixth embodiment.

In an eighth embodiment, the compound is represented by Formula (I), (II) or (III), or a pharmaceutically acceptable salt thereof, wherein:

$R^1$ in each occurrence is independently selected from H, $C_{1-6}$alkyl, and halo, wherein said $C_{1-6}$alkyl is optionally substituted with one to three $R^{10}$;

$R^{10}$ in each occurrence is independently selected from $C_{1-6}$alkyl, halo, halo$C_{1-6}$alkyl and $C_{3-6}$cycloalkyl, and wherein the values of the other variables are as defined for the first, second, third, fourth, fifth or sixth embodiment.

In a ninth embodiment, the compound is represented by Formula (I), (II) or (III), or pharmaceutically acceptable salt thereof, wherein:

n is 1;

$R^1$ is selected from H, —F, —Cl, —Br, —CF$_3$, and —CH$_3$, and wherein the values of the other variables are as defined for the first, second, third, or fourth embodiment.

In a tenth embodiment, the compound is represented by Formula (I), (II) or (III), or pharmaceutically acceptable salt thereof, wherein:

$R^3$ is selected from $C_{1-6}$alkyl, $C_{2-6}$alkynyl, $C_{3-6}$cycloalkyl and 5- to 6-membered N-containing heteroaryl, wherein said $C_{1-6}$alkyl, $C_{2-6}$alkynyl, $C_{3-6}$cycloalkyl and 5- to 6-membered N-containing heteroaryl are optionally substituted with one to three $R^{30}$;

$R^{30}$ in each occurrence is independently selected from $C_{1-6}$alkyl, phenyl, $C_{3-6}$cycloalkyl, 5- to 6-membered N-containing heteroaryl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —O$R^{30a}$, and —OC(O)$R^{30a}$, wherein said $C_{1-6}$alkyl, phenyl, $C_{3-6}$cycloalkyl, and 5- to 6-membered N-containing heteroaryl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, phenyl, and 5- to 6-membered N-containing heteroaryl, wherein said $C_{1-6}$alkyl, phenyl, and 5- to 6-membered N-containing heteroaryl is optionally substituted with one to three $C_{1-4}$alkyl or halo; and the values of the other variables are as defined in the first, second, third, fourth, fifth, sixth, seventh, eighth or ninth embodiment.

In an eleventh embodiment, the compound is represented by Formula (I), (II) or (III), or pharmaceutically acceptable salt thereof, wherein:

$R^3$ is $C_{1-6}$alkyl or $C_{3-6}$cycloalkyl, wherein said $C_{1-6}$alkyl and $C_{3-6}$cycloalkyl are each optionally substituted with one to three $R^{30}$;

$R^{30}$ in each occurrence is independently $C_{1-6}$alkyl or halo, wherein said $C_{1-6}$alkyl is optionally substituted with one to three halo, and wherein the values of the other variables are as defined in the first, second, third, fourth, fifth, sixth, seventh, eighth, ninth or tenth embodiment.

In a twelfth embodiment, the compound is represented by Formula (I), (II) or (III), or pharmaceutically acceptable salt thereof, wherein:

$R^3$ is —CH(CH$_3$)CF$_3$, —CH(CH$_3$)CHF$_2$, —CH(CH$_3$)$_2$, —CH(CH$_3$)CH(CH$_3$)$_2$, cyclopropyl, or cyclobutyl, wherein said cyclopropyl and cyclobutyl are optionally substituted with one or two fluoro or —CF$_3$, and wherein the values of the other variables are as defined in the first, second, third, fourth, fifth, sixth, seventh, eighth, ninth or tenth embodiment.

In a thirteenth embodiment, the compound is represented by the Formula (IV):

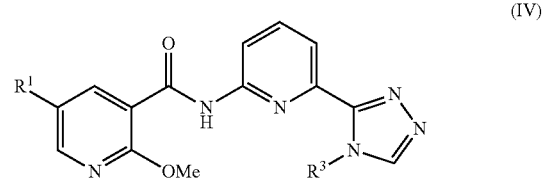

(IV)

or a pharmaceutically acceptable salt thereof, wherein:

$R^1$ is H, halo, or $C_{1-6}$alkyl; and $R^3$ is $C_{1-6}$alkyl or $C_{3-6}$cycloalkyl, wherein said $C_{1-6}$alkyl and $C_{3-6}$cycloalkyl are optionally substituted with one to three fluoro, $C_{1-4}$alkyl or halo$C_{1-4}$alkyl.

In a fourteenth embodiment, the compound is represented by Formula (IV), or a pharmaceutically acceptable salt thereof, wherein:

$R^3$ is $C_{1-3}$alkyl, cyclopropyl or cyclobutyl, wherein said $C_{1-3}$alkyl, cyclopropyl and cyclobutyl are optionally substituted with one or two substituents independently selected from fluoro, $C_{1-3}$alkyl and halo$C_{1-3}$alkyl, and wherein the values of the other variables are as defined in the thirteenth embodiment.

In a fifteenth embodiment, the compound is represented by Formula (IV), or a pharmaceutically acceptable salt thereof, wherein:

$R^1$ is H, —F, —Cl, —Br, or —CH$_3$; and
$R^3$ is —CH(CF$_3$)CH$_3$, —CH(CHF$_2$)CH$_3$, or —CH(CH$_2$F)CH$_3$.

In a sixteenth embodiment, the compound is represented by Formula (IV), or a pharmaceutically acceptable salt thereof, wherein:

$R^1$ is H, —F, —Cl, —Br, or —CH$_3$; and
$R^3$ is cyclopropyl or cyclobutyl, wherein said cyclopropyl and cyclobutyl are optionally substituted with one or two substituents independently selected from fluoro and —CF$_3$.

In a seventeenth embodiment, the compound is represented by Formula (IV), or a pharmaceutically acceptable salt thereof, wherein:

$R^1$ is H, —F, —Cl, —Br, or —CH$_3$; and
$R^3$ is

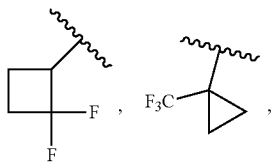 [SMILES: *C1CCC1(F)F ; *C1(C(F)(F)F)CC1]

—CH(CF$_3$)CH$_3$, or —CH(CH$_3$)$_2$.

In an eighteenth embodiment, the compound is represented by Formula (IV), or a pharmaceutically acceptable salt thereof, wherein:

$R^1$ is H, —F, —Cl, —Br, or —CH$_3$; and
$R^3$ is

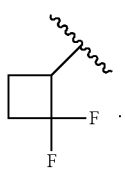 [SMILES: *C1CCC1(F)F]

In a nineteenth embodiment, the compound is represented by Formula (IV), or a pharmaceutically acceptable salt thereof, wherein:

$R^1$ is H, —F, —Cl, —Br, or —CH$_3$; and
$R^3$ is

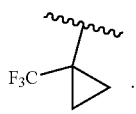

In a twentieth embodiment, the compound is represented by Formula (IV), or a pharmaceutically acceptable salt thereof, wherein:

$R^1$ is H, —F, —Cl, —Br, or —CH$_3$; and
$R^3$ is —CH(CF$_3$)CH$_3$.

In a twenty-first embodiment, the compound is represented by Formula (IV), or a pharmaceutically acceptable salt thereof, wherein:

$R^1$ is H, —F, —Cl, —Br, or —CH$_3$; and
$R^3$ is —CH(CH$_3$)CH$_3$.

In an embodiment, the invention is any one of the compounds disclosed in the Exemplification section as a free compound or a pharmaceutically acceptable salt thereof.

As used herein, unless expressly stated to the contrary or otherwise clear from context, the term "include" and its variations ("includes", "including", etc.) are intended to be non-limiting. That is, unless expressly stated to the contrary or otherwise clear from context, "include" means "include but are not limited to", and so on.

As used herein, the term "alkyl" refers to a saturated branched or unbranched hydrocarbon moiety. Preferably the alkyl comprises 1 to 6 carbon atoms, or 1 to 4 carbon atoms. In some embodiments, an alkyl comprises from 6 to 20 carbon atoms. Examples of alkyl include methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more. Examples of alkenyl groups include ethenyl, n-propenyl, isopropenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, propynyl, but-2-ynyl, n-hex-3-ynyl and the like.

The number of carbon atoms in a group is specified herein by the prefix "$C_{x\text{-}xx}$", wherein x and xx are integers. For example, "$C_{1\text{-}4}$alkyl" is an alkyl group which has from 1 to 4 carbon atoms.

"Halogen" or "halo" may be fluoro, chloro, bromo or iodo.

As used herein, the term "heterocyclyl" refers to (1) a saturated or unsaturated, monocyclic or bicyclic (e.g., bridged or spiro ring systems) ring system which has from 3 to 10 ring members, or in particular 3 to 8 ring members, 3 to 7 ring members, 3 to 6 ring members or 5 to 7 ring members or 4 to 7 ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and/or sulfone; or (2) a heteroaryl group. As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring or a 4- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or -7-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

In one embodiment, a heterocyclyl is a 4- to 7-membered monocyclic heterocyclyl. Examples of 4- to 7-membered monocyclic heterocyclic ring systems include azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl.

As used herein, a "4- to 7-membered monocyclic non-aromatic heterocyclyl" is a monocyclic heterocyclyl having 4- to 7-ring members and is saturated or partially unsaturated (i.e., non-aromatic). Examples of 4- to 7-membered monocyclic non-aromatic heterocyclyls include azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, azepanyl, oxepanyl, thiepanyl, dihydrofuranyl, imidazolinyl, and dihydropyranyl.

As used herein, "6- to 8-membered spiro or bridged bicyclic heterocyclyl" refers to a bicyclic heterocyclyl ring that is a bridged or spiro ring system having total of 6 to 8 ring members. Examples of 6- to 8-membered spiro or bridged bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, 3-oxa-8-azabicyclo[3.2.1]octanyl, 6-oxa-3-azabicyclo[3.1.1]heptanyl, 8-oxa-3-azabicyclo[3.2.1]octanyl, 3-oxa-6-azabicyclo[3.1.1]heptanyl, and 5-azaspiro[2.3]hexanyl.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

As used herein, the term "N-containing heterocyclyl" or "N-containing heteroaryl" refers to a heterocyclyl or a heteroaryl containing at least one N as ring atom. The N-containing heterocyclyl group or the N-containing heteroaryl group can be attached at a N or a carbon atom. A "4- to 7-membered monocyclic non-aromatic heterocyclyl" is a saturated or partially unsaturated N-containing heterocyclyl that is monocyclic. Examples of 4- to 7-membered monocyclic non-aromatic heterocyclyl include azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, azepanyl, and imidazolinyl. A "5- to 6-membered N-containing heteroaryl" is a N-containing heteroaryl containing 5- or 6-ring members. Examples of 5- to 6-membered N-containing heteroaryl include imidazolyl, pyrazolyl, oxazolyl, isoxazolyl, thiazolyl, isothiazolyl, oxadiazolyl, thiadiazolyl, triazolyl, tetrazolyl, pyridinyl, pyrazinyl, pyrimidinyl, pyridazinyl, triazinyl, tetrazinyl and the like.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to saturated monocyclic or bicyclic or spiro hydrocarbon groups of 3-7 carbon atoms, 3-6 carbon atoms, or 5-7 carbon atoms. Exemplary monocyclic carbocyclyl groups include cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo [2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases can include sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri (substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and triamines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Examples of amines can include isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. Other carboxylic acid derivatives can be useful, for example, carboxylic acid amides, including carboxamides, lower alkyl carboxamides, dialkyl carboxamides, and the like.

The compounds or pharmaceutically acceptable salts thereof as described herein, can contain one or more asymmetric centers in the molecule. In accordance with the present disclosure, any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). When a particular stereoisomer of a compound used in the disclosed methods is depicted by name or structure, the stereochemical purity of the compound is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers. When a particular stereoisomer of a compound used in the disclosed methods is depicted by name or structure as indicating a single enantiomer, the enantiomeric purity of the compound is at least 60%, 70%, 80%, 90%, 95%, 97%, 99%, 99.5% or 99.9%. "Enantiomeric purity" means the weight percent of the desired stereoisomer relative to the combined weight of the desired stereoisomer and its enantiomer.

The disclosed compounds may exist in tautomeric forms and mixtures and separate individual tautomers are contemplated. In addition, some compounds may exhibit polymorphism.

In some embodiments, the compounds of the invention or a pharmaceutically acceptable salt thereof include deuterium in greater than natural abundance.

Another embodiment is a pharmaceutical composition comprising at least one compound described herein, or a pharmaceutically acceptable salt thereof, and at least one pharmaceutically acceptable carrier or excipient.

The compounds, or pharmaceutically acceptable salts thereof described herein may be used to decrease the activity of ASK1, or to otherwise affect the properties and/or behavior of ASK1, e.g., stability, phosphorylation, kinase activity, interactions with other proteins, etc.

One embodiment of the invention includes a method of treating a disorder responsive to inhibition of ASK1 in a subject comprising administering to said subject an effective amount of at least one compound described herein, or a pharmaceutically acceptable salt thereof.

Studies have demonstrated that ASK1 is involved in ROS- or ER stress-related disease mechanisms, suggesting its therapeutic role in various human diseases. The accumulation of misfolded proteins in the endoplasmic reticulum induces ER stress, leading to the disturbance of ER function. Unfolded-protein response (UPR) is the ER quality control system to restore function. Apoptosis signaling is induced with prolonged ER stress or malfunction of the UPR. The role for ASK1 activation in neurodegenerative disease involves both ER and oxidative stress mechanisms.

In some embodiments, the disorders responsive to inhibition of ASK1 include neurodegenerative disorders, cardiovascular diseases, metabolic (e.g. diabetes) disorders, inflammatory diseases, damage following ischemia, autoimmune disorders, destructive bone disorders, polyglutamine diseases, glutamate neurotoxicity, pain, traumatic brain injury, hemorrhagic stroke, ischemia, acute hypoxia, kidney fibrosis (renal fibrosis), kidney injury (Terada et al., Biochem Biophys Res Commun. 2007, 364(4), 1043-92007), diabetic kidney disease/diabetic nephropathy, non-alcoholic steatohepatitis (NASH), pulmonary arterial hypertension (PAH), optic neuritis, liver diseases, respiratory diseases (chronic obstructive pulmonary disease COPD, lung injury), heart reperfusion injury (Gerczuk P Z et al., J Cardiovasc Pharmacol. 2012, 60(3), 276-82), cardiac hypertrophy, cardiac fibrosis (Yamaguchi et al., J Clin Invest. 2004, 114(7), 937-43), energy metabolic disorders, cancers (such as liver cancer, gastric cancer (Hayakawa et al., Proc Natl Acad Sci USA. 2011, 108(2), 780-5), and infection (e.g. sepsis).

In some embodiments, the invention provides a method for treating a neurodegenerative disease. In some embodiments, the neurodegenerative diseases include Alzheimer's disease, hippocampal sclerosis, frontotemporal dementia (FTD), frontotemporal lobar degeneration (FTLD), Huntington's disease, corticobasal degeneration, amyotrophic lateral sclerosis, spinal muscular atrophy, motor neuron disease, inclusion body myositis, Parkinson's disease, dementia with Lewy bodies, Lewy body disease, multiple system atrophy, progressive supranuclear palsy, Pick's disease, prion diseases, traumatic brain injury, ischemic and hemorrhagic stroke, cerebral ischemia, hypoxia, and glutamate neurotoxicity. In some embodiments, the neurodegenerative disease is selected from Alzheimer's disease (AD), Parkinson's disease, Huntington's disease, and amyotrophic lateral sclerosis (ALS).

ALS is a progressive neurodegenerative disease that affects nerve cells in the brain and spinal cord. The progressive degeneration of motor neurons in ALS eventually leads to their death. When motor neurons die, the ability of the brain to initiate and control muscle movement is lost. With voluntary muscle action progressively affected, people may lose the ability to speak, eat, move, and breathe. Patients in the later stages of the disease may become totally paralyzed.

In vitro studies show that ASK1 is required for Fas receptor induced death of mouse primary motor neurons, and mutSOD1 motor neurons demonstrate increased susceptibility (Raoul et al., Neuron. 2002, 35(6), 1067-83). Mutant SOD1 protein causes motor neuron death through activation of ASK1. Activation of the ASK1 pathway is increased in mutSOD1 motor neurons, and is active early in SOD1 mouse disease progression (Wengenack et al., Brain Res. 2004, 1027(1-2), 73-86; Holsek et al., Brain Res. 2005, 1045(1-2), 185-98). In cells, ASK1 mediates cytotoxic signaling in mutSOD1 expressing cells, and the protective effect of pro-survival pathways in mutSOD1 motor neurons involves inhibition of ASK1 (Pevani et al., Mol Neurobiol. 2014, 49(1):136-48).

In transgenic mouse studies, both genetic deletion (Nishitoh et al., Genes and Dev 2008, 22(11), 1451-64) and pharmacological inhibition of ASK1 (Fujisawa et al., Hum. Mol. Genet. 2016, 25(2), 245-53) has demonstrated reduced motor neuron loss and increased/extended lifespan, as well as reduced neuroinflammation in the SOD1_G93A transgenic mouse model of ALS.

Parkinson's disease is a disorder of the nervous system that results from the loss of cells in various parts of the brain, including a region called the substantia nigra. The sustantia nigra cells produce dopamine, a chemical messenger responsible for transmitting signals within the brain that allow for coordination of movement. Loss of dopamine causes neurons to fire without normal control, leaving patients less able to direct or control their movement. Parkinson's disease is one of several diseases categorized by clinicians as movement disorders.

In the mitochondrial complex 1 inhibitor MPTP (1-methyl-4-phenyl-1,2,3,6-tetrahydro-pyridine) model of dopaminergic cell loss, ASK1 deficient mice are shown to be relatively resistant to MPTP lesions. MPTP-induced dopamine neuron toxicity and motor impairment is also attenuated in ASK1 knock-out mice, as is neuroinflammation, suggesting protective effects of ASK1 inhibition (Lee et al., PlosOne 2012; 7(1), e29935). Abolishing ASK activity in another MPTP model also attenuated dopaminergic cell loss (Karunakaran et al., FASEB J. 2007, 21(9), 2226-36).

Accumulation of pathogenic proteins such as alpha-synuclein, in alpha-synucleopathies including Parkinson's disease, and its overexpression and aggregation in model systems is associated with neuroinflammation and increased oxidative stress. AlphaSynuclein transgenic mice deficient in ASK1 demonstrate improved motor function (Lee et al., NeuroBiolAging 2015, 36(1), 519-26).

Further, in 6-hydroxydopamine (6-OHDA, a toxin that causes dopaminergic cell loss) models, attenuating the ASK1 signaling cascade provides protection against dopaminergic neuron loss (Hu et al., J Neurosci. 2011, 31(1), 247-61).

Alzheimer's disease (AD) is a type of dementia that causes problems with memory, thinking and behavior. In AD the brain cells degenerate and die, causing a steady decline in memory and mental function. AD is characterized by increased levels of amyloid-beta (ABeta) peptides and hyper-phosphorylated Tau which lead to the hallmark pathologies ABeta-amyloid plaques and Tau tangles.

ASK1 activation may be associated with AD. Neurons treated with toxic ABeta peptides demonstrate increased toxicity due to oxidative stress (ROS). Exposure to ABeta peptides leads to ASK1 activation (Wang et al., J Mol Neurosci. 2015, 55(1), 227-32). ABeta-induced neuronal death via ROS-mediated ASK1 activation is a key mechanism for ABeta-induced neurotoxicity (Kadowaki et al., Cell Death Differ. 2005, 12(1), 19-24). ASK1 is also required for ROS-induced JNK activation and apoptosis.

Huntington's disease is an inherited disease that causes the progressive breakdown (degeneration) of nerve cells in the brain. Huntington's disease has a broad impact on a person's functional abilities and usually results in movement, thinking (cognitive) and psychiatric disorders. Mutations in the HTT gene cause Huntington's disease. The HTT gene provides instructions for making a protein called huntingtin. Although the function of this protein is unknown, it appears to play an important role in nerve cells (neurons) in the brain.

The HTT mutation that causes Huntington's disease involves a DNA segment known as a CAG trinucleotide repeat. This segment is made up of a series of three DNA building blocks (cytosine, adenine, and guanine) that appear multiple times in a row. Normally, the CAG segment is repeated 10 to 35 times within the gene. In people with Huntington's disease, the CAG segment is repeated 36 to more than 120 times. People with 36 to 39 CAG repeats may or may not develop the signs and symptoms of Huntington's disease, while people with 40 or more repeats almost always develop the disorder. During protein synthesis, the expanded CAG repeats are translated into a series of uninterrupted glutamine residues forming what is known as a polyglutamine tract ("polyQ"). Such polyglutamine tracts may be subject to increased aggregation.

Studies have shown that ASK1 is essential for endoplasmic reticulum stress-induced neuronal cell death triggered by expanded polyglutamine repeats. (Nishitoh et al., Genes Dev. 2002, 16(11), 1345-55).

Another embodiment of the invention includes a method for treating an autoimmune disease in a subject comprising administering to the subject a therapeutically effective amount of a compound disclosed herein, or a pharmaceutically acceptable salt thereof.

In some embodiments, the autoimmune disease is selected from rheumatoid arthritis, systemic lupus erythematosus, multiple sclerosis, diabetes, systemic sclerosis, Grave's disease, Guillain-Barre syndrome, myasthenia gravis, psoriasis, Crohn's disease, ulcerative colitis, optic neuritis, and Sjogren's syndrome.

In some embodiments, the autoimmune disease is multiple sclerosis (MS).

Multiple sclerosis (MS) involves an immune-mediated process in which an abnormal response of the body's immune system is directed against the central nervous system (CNS), which is made up of the brain, spinal cord and optic nerves. The immune system attacks myelin, which surrounds and insulates nerve fibers. When myelin is damaged, scar tissue is formed (sclerosis) which gives the disease its name. Twenty percent of MS patients initially present with optic neuritis, and 30-70% of MS patients develop optic neuritis during the course of disease (loss of visual acuity, which can lead to neuromyelitis optica, severe and irreversible visual loss). Optic neuritis is inflammation of the optic nerve, which is the most common form of optic neuropathy.

In experimental autoimmune encephalomyelitis (EAE) models of inflammation, demyelination, and axonal degeneration, the severity of EAE is reduced in ASK1 deficient mice, as well as mice treated with ASK1 inhibitors. Inhibitors of ASK1 suppressed EAE-induced inflammation in both the spinal cord and optic nerves, suggesting the TLR-ASK1-p38 pathway may serve as a therapeutic target for immune-related demyelinating disorders (Guo et al., EMBOMol. Med. 2 (2010) 504-515; Azuchi et al., Neurosci Lett. 2017, 639, 82-87).

In some embodiments, the invention provides a method of treating a cardiovascular disease in a subject comprising administering to the subject a therapeutically effective amount of a compound disclosed herein, or a pharmaceutically acceptable salt thereof.

Cardiovascular diseases refer to diseases of the cardiovasculature (heart and blood vessels) arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, atherosclerosis, and intermittent claudication. Cardiovascular diseases also include diseases associated with malfunction of heart valves which do not allow sufficient amount of blood to flow through (such as valvular stenosis, valvular insufficiency or regurgitation, congenital valve disease, bicuspid aortic valve disease, or acquired valve disease).

Stroke occurs when blood flow to an area of the brain is cut off. When this happens, brain cells are deprived of oxygen and begin to die. A hemorrhagic stroke is either a brain aneurysm burst or a weakened blood vessel leak. Intracerebal hemorrhage, a more common hemorrhagic stroke, happens when a blood vessel inside the brain bursts and leaks blood into surrounding brain tissue. Subarachnoid hemorrhage involves bleeding in the area between the brain and the tissue covering the brain, known as the subarachnoid space. This type of stroke is most often caused by a burst aneurysm. Cerebral (or brain) ischemia is a condition that occurs when there is not enough blood flow to the brain to meet metabolic demand, and can be considered a subtype of stroke. This results in limited oxygen supply or cerebral hypoxia and leads to the death of brain tissue, cerebral infarction, or ischemic stroke. Ischemic stroke occurs when a blood vessel carrying blood to the brain is blocked by a blood clot. Embolic and thrombotic stroke are ways in which an ischemic stroke can occur. In an embolic stroke, a blood clot or plaque fragment forms somewhere in the body (usually the heart) and travels to the brain. Once in the brain, the clot travels to a blood vessel small enough to block its passage. A thrombotic stroke is caused by a blood clot that forms inside one of the arteries supplying blood to the brain.

In some embodiments, the invention provides a method of treating stroke in a subject comprising administering to the subject a therapeutically effective amount of a compound disclosed herein, or a pharmaceutically acceptable salt thereof.

Traumatic brain injury (TBI), a form of acquired brain injury, occurs when a sudden trauma causes damage to the brain. Because little can be done to reverse the initial brain damage caused by trauma, medical personnel try to stabilize an individual with TBI and focus on preventing further injury. Primary concerns include insuring proper oxygen supply to the brain and the rest of the body, maintaining adequate blood flow, and controlling blood pressure.

In some embodiments, the invention provides a method of treating traumatic brain injury in a subject comprising administering to the subject a therapeutically effective amount of a compound disclosed herein, or a pharmaceutically acceptable salt thereof.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

In another embodiment, the invention provides a method for treating ischemia in a subject comprising administering to the subject a therapeutically effective amount of a compound disclosed herein, or a pharmaceutically acceptable salt thereof.

Activation of ASK1 by reactive oxygen species (ROS) has been linked to vascular injury and neuronal death following cerebral ischemia. Studies show that induction of ASK1 expression promotes apoptotic cell death following ischemia and silencing ASK1 expression reduces cerebral infarction in the brain (Kim et al Brain Res. 2011, 1412, 73-78). The inhibition of ASK1 has been shown to exert protective effects in ischemia induced brain edema (Song et al., Brain Res. 2015, 1595, 143-155). Preventing ASK1 activation in a cerebral ischemia-reperfusion model is also shown to exert neuroprotection (Liu et al., Neuroscience. 2013, 229, 36-48). In a middle cerebral artery (MCA) occlusion model, ASK1 inhibition showed decreased neuronal death as well as in hypoxia/reperfusion injury models (Cheon et al., Front Cell Neurosci. 2016, 10, 213).

In one embodiment, the invention provides a method for treating liver injury in a subject comprising administering to the subject a therapeutically effective amount of a compound disclosed herein, or a pharmaceutically acceptable salt thereof.

Acetaminophen (APAP) overdose is the most common form of drug-induced liver injury. JNK activation is a consequence of oxidative stress produced during APAP metabolism, resulting in hepatocyte damage with necrotic and apoptotic cell death. (Nakagawa et al., Gastroenterology. 2008, 135(4), 1311-21). It has been shown that ASK1 inhibitors protect against APAP induced liver injury (Xie et al., Toxicol Appl Pharmacol. 2015, 286(1), 1-9; He et al., Asian Pac J Trop Med. 2016, 9(3), 283-7).

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant. Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound or a pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

Example 1: N-(6-(4-Isopropyl-4H-1,2,4-triazol-3-yl)pyridin-2-yl)-2-methoxynicotinamide

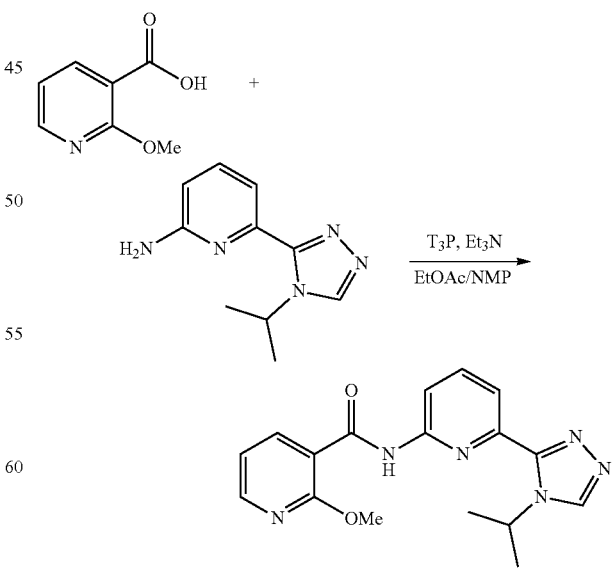

A 2-dram vial was charged with 2-methoxynicotinic acid (37 mg, 0.18 mmol). A stock solution of 6-(4-isopropyl-4H-

1,2,4-triazol-3-yl)pyridin-2-amine (17 mg, 0.08 mmol) in N-methyl-2-pyrrolidone and EtOAc (1:1 Vol %, 0.8 mL) and triethylamine (0.15 mL, 1.09 mmol) was prepared and added to the vial, followed by a T₃P (propylphosphonic anhydride) solution (≥50 wt % in EtOAc, 0.32 mL, 0.54 mmol). The reaction solution was heated at 60° C. for 16 h and after this time the mixture was cooled to rt and diluted with water and EtOAc (1:1 Vol %, 4 mL). The separated aqueous layer was extracted with EtOAc (×2) and the combined organic extracts were evaporated to yield a solid. This crude material was subjected to reverse phase HPLC (using a Waters SunFire Prep C18 OBD, 5 μm, 19×100 mm column and using water/CH₃CN (containing 0.1% TFA) from 95/5 to 30/70 as the mobile phase at a flow rate of 30 mL/min) to give the title compound (17.2 mg, 27%) as a slightly yellow solid. MS (ESI): 339.1 [M+H]⁺.

Example 2: 2-Hydroxy-N-(6-(4-isopropyl-4H-1,2,4-triazol-3-yl)pyridin-2-yl)nicotinamide

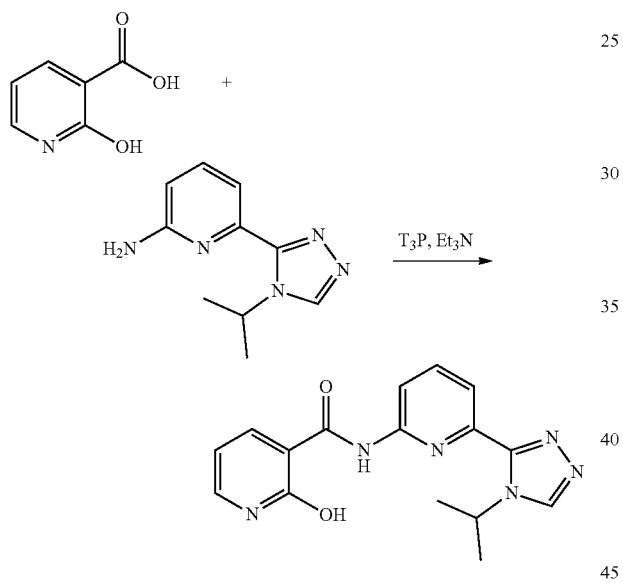

To a mixture of 6-(4-isopropyl-1,2,4-triazol-3-yl)pyridin-2-amine (32 mg, 0.16 mmol) and 2-oxo-1H-pyridine-3-carboxylic acid (23 mg, 0.17 mmol) in a microwave reaction vessel equipped with a magnetic stirring bar was added triethylamine (0.26 mL, 1.9 mmol) and propylphosphonic anhydride (≥50 wt % in EtOAc, 0.26 mL). The mixture was heated in a microwave reactor at 110° C. for 1.5 h. After this time the mixture was quenched with a small amount of MeOH (~1 mL) and then it was partitioned between EtOAc and water. The aqueous layer was extracted with EtOAc and the combined organic extracts were dried over MgSO₄, filtered and concentrated in vacuo. The crude product was triturated with MeOH/water (2/1, 1 mL) and dried under vacuum to give the title compound (6.8 mg, 13%) as a red-brown solid. ¹H NMR (400 MHz, CD₃OD) δ ppm 8.85 (s, 1H), 8.67 (dd, J=7.40, 2.13 Hz, 1H), 8.46 (d, J=7.78 Hz, 1H), 8.02 (t, J=8.03 Hz, 1H), 7.88 (d, J=7.03 Hz, 1H), 7.79 (dd, J=6.27, 2.01 Hz, 1H), 6.68 (dd, J=7.15, 6.40 Hz, 1H), 5.49-5.71 (m, 1H), 1.64 (d, J=6.78 Hz, 6H). MS (ESI): 325.0 [M+H]⁺.

Example 3: N-(6-(4-Cyclobutyl-4H-1,2,4-triazol-3-yl)pyridin-2-yl)-2-methoxynicotinamide

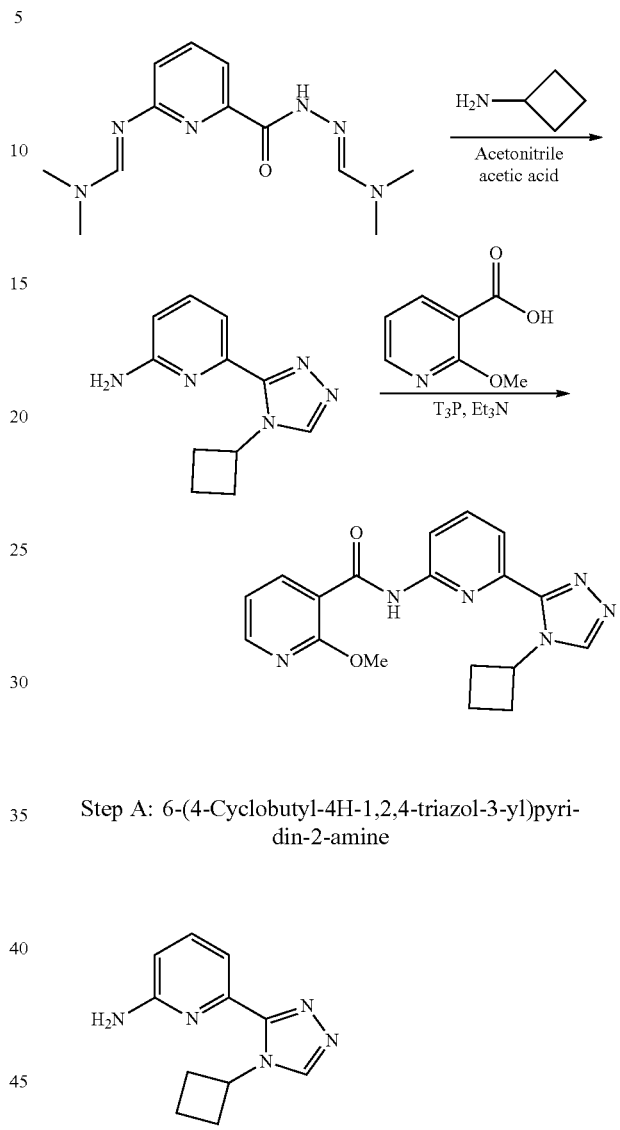

Step A: 6-(4-Cyclobutyl-4H-1,2,4-triazol-3-yl)pyridin-2-amine

To a mixture of (E)-N'-(6-(2-((E)-(dimethylamino)methylene)hydrazine-1-carbonyl)pyridin-2-yl)-N,N-dimethylformimidamide (263 mg, 1.0 mmol) and cyclobutanamine (0.17 mL, 2.0 mmol) in a microwave reaction vessel equipped with a magnetic stirring bar was added acetonitrile (3 mL), followed by acetic acid (1 mL). The mixture was heated in a hot plate at 120° C. for 24 h. After this time the reaction was cooled to rt and partitioned between EtOAc and NaHCO₃ (saturated aqueous solution). The separated aqueous layer was extracted with EtOAc and the combined organic extracts were dried over MgSO₄, filtered and concentrated. The residue was purified by normal phase column eluting with 100% EtOAc to give the title compound (188 mg, 87%). ¹H NMR (400 MHz, CD₃OD) δ ppm 8.79 (s, 1H), 7.55 (dd, J=8.28, 7.53 Hz, 1H), 7.17 (d, J=7.28 Hz, 1H), 6.64 (d, J=8.28 Hz, 1H), 5.38-5.59 (m, 1H), 2.48-2.67 (m, 2H), 2.39 (quind, J=9.57, 9.57, 9.57, 9.57, 2.64 Hz, 2H), 1.79-1.99 (m, 2H). MS (ESI): 216.0 [M+H]⁺.

Step B: N-(6-(4-Cyclobutyl-4H-1,2,4-triazol-3-yl)pyridin-2-yl)-2-methoxynicotinamide Step A: (S)-6-(4-(3-Methylbutan-2-yl)-4H-1,2,4-triazol-3-yl)pyridin-2-amine

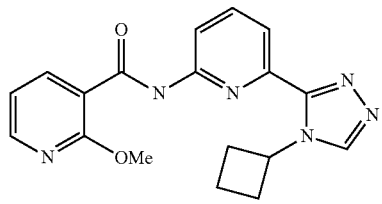 [SMILES: COc1ncccc1C(=O)Nc1cccc(-c2nncn2C2CCC2)n1]

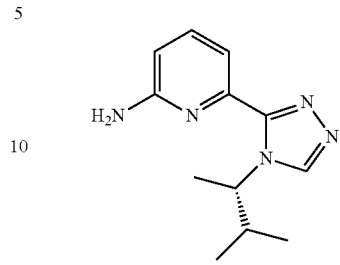

To a mixture of 6-(4-cyclobutyl-4H-1,2,4-triazol-3-yl)pyridin-2-amine (30 mg, 0.14 mmol) and 2-methoxypyridine-3-carboxylic acid (24 mg, 0.15 mmol) in a microwave reaction vessel equipped with a magnetic stirring bar was added triethylamine (0.25 mL, 1.80 mmol) and propylphosphonic anhydride (≥50 wt % in EtOAc, 0.25 mL). The mixture was heated in a microwave reactor at 110° C. for 1 h. After this time the reaction was quenched with a small amount of MeOH (1 mL). The solid was filtered and washed with EtOAc (1 mL) and dried under vacuum to give the title compound (25 mg, 51%) as an off-white solid. $^1$H NMR (400 MHz, CD$_3$OD) δ ppm 8.89 (s, 1H), 8.43-8.56 (m, 2H), 8.40 (dd, J=4.77, 2.01 Hz, 1H), 8.01 (t, J=8.03 Hz, 1H), 7.87 (d, J=7.28 Hz, 1H), 7.21 (dd, J=7.53, 4.77 Hz, 1H), 5.53 (s, 1H), 5.21-5.78 (m, 1H), 4.22 (s, 3H), 2.60-2.77 (m, 2H), 2.52 (td, J=9.73, 2.38 Hz, 2H), 1.79-2.10 (m, 2H). MS (ESI): 350.9 [M+H]$^+$.

Example 4: (S)-2-Methoxy-N-(6-(4-(3-methylbutan-2-yl)-4H-1,2,4-triazol-3-yl)pyridin-2-yl)nicotinamide To a mixture of (E)-N'-(6-(2-((E)-(dimethylamino)methylene)hydrazine-1-carbonyl)pyridin-2-yl)-N,N-dimethylformimidamide (1.05 g, 4.00 mmol) and (S)-3-methylbutan-2-amine (1.05 mL, 9.06 mmol) in a microwave reaction vessel was added acetonitrile (6 mL), followed by acetic acid (2 mL). The mixture was heated in a hot plate at 120° C. for 24 h. After this time the reaction mixture was partitioned between EtOAc and NaHCO$_3$ (saturated aqueous solution). The aqueous layer was extracted with EtOAc and the combined organic extracts were dried over MgSO$_4$, filtered and concentrated. The product was purified by normal phase column eluting with EtOAc/EtOH (3/1) to give the title compound (802 mg, 87%). $^1$H NMR (400 MHz, CD$_3$OD) δ ppm 8.73 (s, 1H), 7.57 (dd, J=8.28, 7.53 Hz, 1H), 7.17 (d, J=7.03 Hz, 1H), 6.65 (d, J=8.03 Hz, 1H), 5.08-5.34 (m, 1H), 1.96-2.11 (m, 1H), 1.55 (d, J=6.78 Hz, 3H), 30.90-0.97 (m, 3H), 0.67-0.78 (m, 3H). MS (ESI): 232.0 [M+H]$^+$.

Step B: (S)-2-Methoxy-N-(6-(4-(3-methylbutan-2-yl)-4H-1,2,4-triazol-3-yl)pyridin-2-yl)nicotinamide

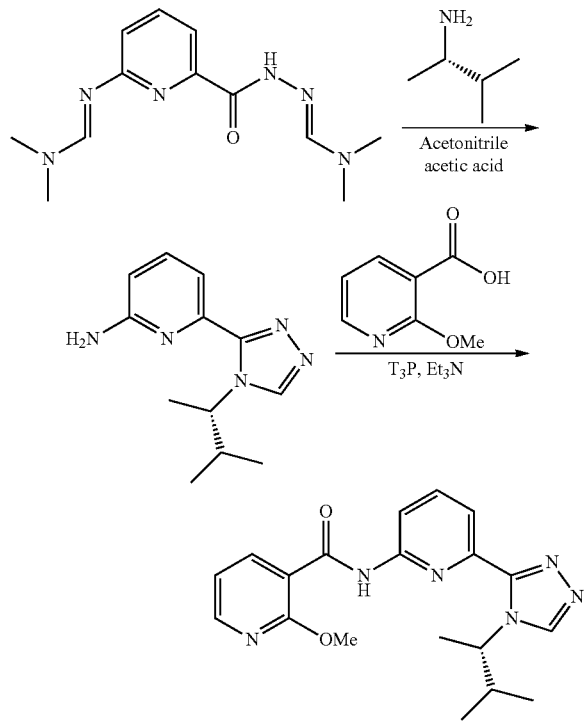

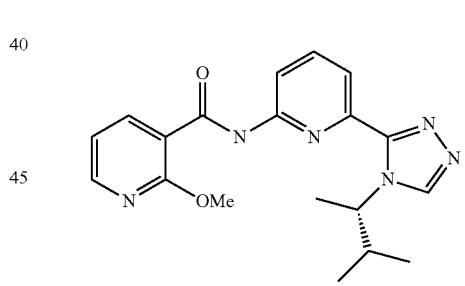

To a mixture of (S)-6-(4-(3-methylbutan-2-yl)-4H-1,2,4-triazol-3-yl)pyridin-2-amine (46 mg, 0.20 mmol) and 2-methoxypyridine-3-carboxylic acid (34 mg, 0.22 mmol) in a microwave reaction vessel equipped with a magnetic stirring bar was added triethylamine (0.32 mL, 2.33 mmol) and propylphosphonic anhydride (≥50 wt % in EtOAc, 0.32 mL). The mixture was heated in a microwave reactor at 110° C. for 1.5 h. After this time the reaction was quenched with a small amount of MeOH (~1 mL) and then it was partitioned between EtOAc and NaHCO$_3$ (sat. aq. solution). The separated organic phase was dried over MgSO$_4$, filtered and concentrated in vacuo. The product was purified by column chromatography on silica gel using a gradient of elution EtOAc/EtOH (7/1) to give the title compound (35 mg, 48%) as a white solid. $^1$H NMR (400 MHz, CD$_3$OD) δ ppm 8.81-8.93 (m, 1H), 8.42-8.56 (m, 2H), 8.28-8.42 (m, 1H), 7.95-8.10 (m, 1H), 7.78-7.91 (m, 1H), 7.06-7.33 (m, 1H), 5.11-5.37 (m, 1H), 4.20 (s, 3H), 2.01-2.34 (m, 1H), 1.63 (d, J=6.78 Hz, 3H), 1.02 (d, J=6.78 Hz, 3H), 0.82 (d, J=6.78 Hz, 3H). MS (ESI): 366.9 [M+H]⁺.

Example 5: 5-Bromo-N-(6-(4-isopropyl-4H-1,2,4-triazol-3-yl)pyridin-2-yl)-2-methoxynicotinamide

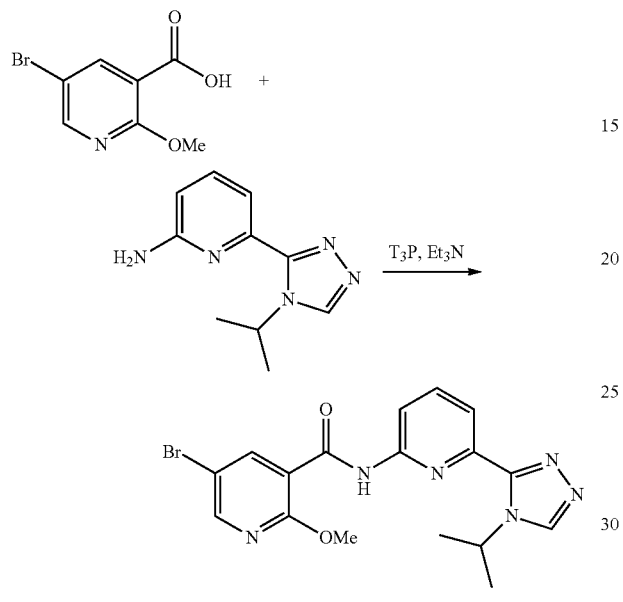

To a suspension of 5-bromo-2-methoxy-pyridine-3-carboxylic acid (232 mg, 1.0 mmol) and 6-(4-isopropyl-1,2,4-triazol-3-yl)pyridin-2-amine (203 mg, 1.0 mmol) in triethylamine (1.52 g, 15.0 mmol, 2.1 mL) was added propylphosphonic anhydride (≥50 wt % in EtOAc, 1.8 mL). The suspension was heated in a hot plate at 80° C. for 1 h (it turned to a clear solution, and then to a suspension again). The reaction was quenched with a small amount of MeOH (~1 mL), and concentrated in vacuo. The residue was triturated with EtOAc (~2 mL) and dried under vacuum to give the title compound (275 mg, 66%) as a pale yellow solid. ¹H NMR (400 MHz, CD₃OD) δ ppm 8.86 (s, 1H), 8.50-8.58 (m, 1H), 8.32-8.50 (m, 2H), 7.95-8.14 (m, 1H), 7.79-7.95 (m, 1H), 5.44-5.69 (m, 1H), 4.18 (s, 3H), 1.63 (d, J=6.53 Hz, 6H). MS (ESI): 417.0 [(M+H) (⁷⁹Br)]⁺.

Example 6: (S)-2-Methoxy-N-(6-(4-(1,1,1-trifluoropropan-2-yl)-4H-1,2,4-triazol-3-yl)pyridin-2-yl)nicotinamide

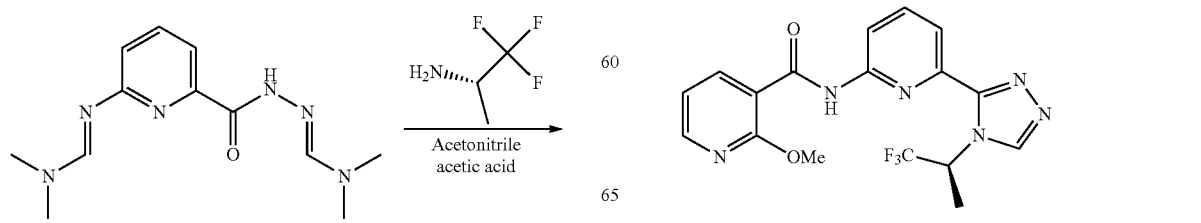

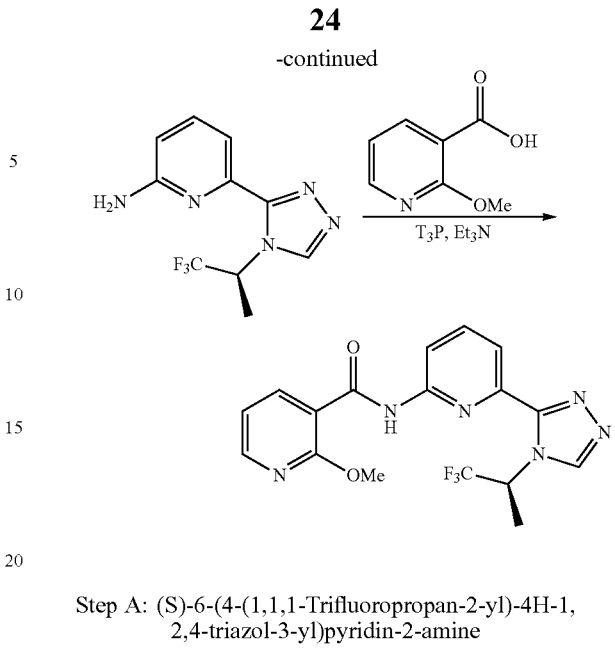

Step A: (S)-6-(4-(1,1,1-Trifluoropropan-2-yl)-4H-1,2,4-triazol-3-yl)pyridin-2-amine (E)-N'-(6-(2-((E)-(Dimethylamino)methylene)hydrazine-1-carbonyl)pyridin-2-yl)-N,N-dimethylformimidamide (1.50 g, 5.72 mmol) and (2S)-1,1,1-trifluoropropan-2-amine (1.45 g, 12.81 mmol) were dissolved in acetonitrile (9 mL). Acetic acid (3 mL) was then added and the resulting mixture was heated in a sealed tube at 120° C. overnight. After this time the reaction was cooled to rt, concentrated in vacuo, dissolved in EtOAc and washed with NaHCO₃ (saturated aqueous solution). The separated organic phase was dried over MgSO₄, filtered and concentrated to give the crude product as a clear oil. Purification by silica gel chromatography (EtOAc) gave the title compound (1.40 g, 95%) as a white solid. ¹H NMR (400 MHz, CD₃OD) δ ppm 8.91 (s, 1H), 7.57 (dd, J=8.4, 7.4 Hz, 1H), 7.34 (dd, J=7.3, 0.8 Hz, 1H), 6.99 (quin, J=7.3 Hz, 1H), 6.65 (dd, J=8.4, 0.9 Hz, 1H), 1.84 (d, J=7.3 Hz, 3H), MS (ESI): 258.2 [M+H]⁺.

Step B. (S)-2-Methoxy-N-(6-(4-(1,1,1-trifluoropropan-2-yl)-4H-1,2,4-triazol-3-yl)pyridin-2-yl)nicotinamide 2-Methoxypyridine-3-carboxylic acid (536 mg, 3.50 mmol) and 6-[4-[(1S)-2,2,2-trifluoro-1-methyl-ethyl]-1,2,4-triazol-3-yl]pyridin-2-amine (900 mg, 3.50 mmol) were dissolved in triethylamine (4.85 mL, 34.99 mmol). Propylphosphonic anhydride (≥50 wt % in EtOAc, 3.6 mL) was added and the reaction was heated at 80° C. for 3 h. The reaction was cooled to rt, quenched with MeOH (10 mL) and stirred for 1 h. The resulting solid was filtered and evaporated in vacuo to give the title compound (865 mg, 63%) as a tan solid. $^1$H NMR (400 MHz, CD$_3$OD) δ 9.04 (d, J=0.75 Hz, 1H), 8.43-8.45 (m, 1H), 8.41-8.43 (m, 1H), 8.39 (dd, J=2.01, 5.02 Hz, 1H), 7.98-8.08 (m, 2H), 7.20 (dd, J=5.02, 7.53 Hz, 1H), 6.94 (quin, J=7.22 Hz, 1H), 4.18 (s, 3H), 1.91 (d, J=7.03 Hz, 3H). MS (ESI): 393.1 [M+H]$^+$.

Example 7: (R)-2-Methoxy-N-(6-(4-(1,1,1-trifluoropropan-2-yl)-4H-1,2,4-triazol-3-yl)pyridin-2-yl)nicotinamide

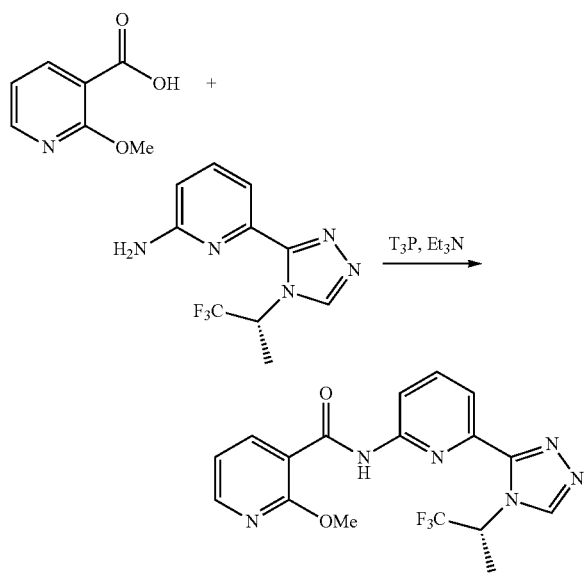

(R)-2-Methoxy-N-(6-(4-(1,1,1-trifluoropropan-2-yl)-4H-1,2,4-triazol-3-yl)pyridin-2-yl)nicotinamide was prepared in an identical manner to that described for (S)-2-methoxy-N-(6-(4-(1,1,1-trifluoropropan-2-yl)-4H-1,2,4-triazol-3-yl)pyridin-2-yl)nicotinamide except (R)-6-[4-[2,2,2-trifluoro-1-methyl-ethyl]-1,2,4-triazol-3-yl]pyridin-2-amine (125 mg) was used instead of the (S) isomer. Filtration of the resulting solid afforded the desired compound as a tan solid (129 mg, 67%). $^1$H NMR (400 MHz, CD$_3$OD) δ 9.04 (s, 1H), 8.35-8.50 (m, 3H), 7.94-8.12 (m, 2H), 7.21 (dd, J=5.02, 7.53 Hz, 1H), 6.94 (quin, J=7.22 Hz, 1H), 4.19 (s, 3H), 1.91 (d, J=7.28 Hz, 3H). MS (ESI): 393.1 [M+H]$^+$.

Example 8: (S)-5-Bromo-2-methoxy-N-(6-(4-(1,1,1-trifluoropropan-2-yl)-4H-1,2,4-triazol-3-yl)pyridin-2-yl)nicotinamide

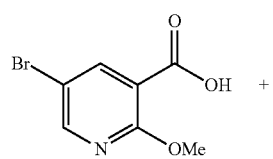

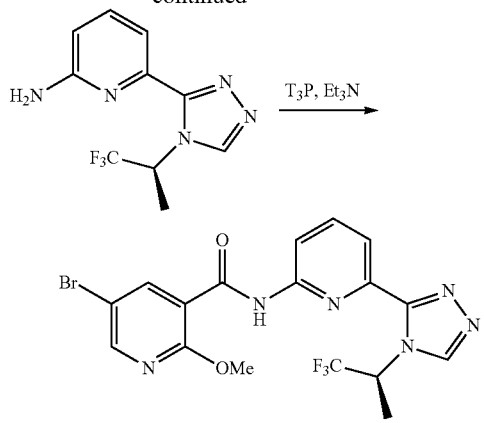

5-Bromo-2-methoxy-pyridine-3-carboxylic acid (162 mg, 0.70 mmol) and 6-[4-[(1S)-2,2,2-trifluoro-1-methyl-ethyl]-1,2,4-triazol-3-yl]pyridin-2-amine (180 mg, 0.70 mmol) were dissolved in triethylamine (1.1 mL, 7.78 mmol). Propylphosphonic anhydride (≥50 wt % in EtOAc, 0.70 mL) was added and the stirred reaction mixture was heated at 80° C. for 3 h. The reaction was cooled to rt and quenched by addition of MeOH (5 mL). The resulting solid was filtered and evaporated in vacuo to give the title compound (130 mg, 39%) as a white solid. $^1$H NMR (400 MHz, CD$_3$OD) δ 9.01 (s, 1H), 8.45 (br d, J=5.52 Hz, 2H), 8.38 (br d, J=7.78 Hz, 1H), 7.95-8.09 (m, 2H), 6.91 (td, J=7.34, 14.43 Hz, 1H), 4.14 (s, 3H), 1.88 (d, J=7.03 Hz, 3H). MS (ESI): 471.0 [(M+H) ($^{79}$Br)]$^+$.

Example 9: rac-5-Bromo-2-methoxy-N-(6-(4-(1,1,1-trifluoropropan-2-yl)-4H-1,2,4-triazol-3-yl)pyridin-2-yl)nicotinamide

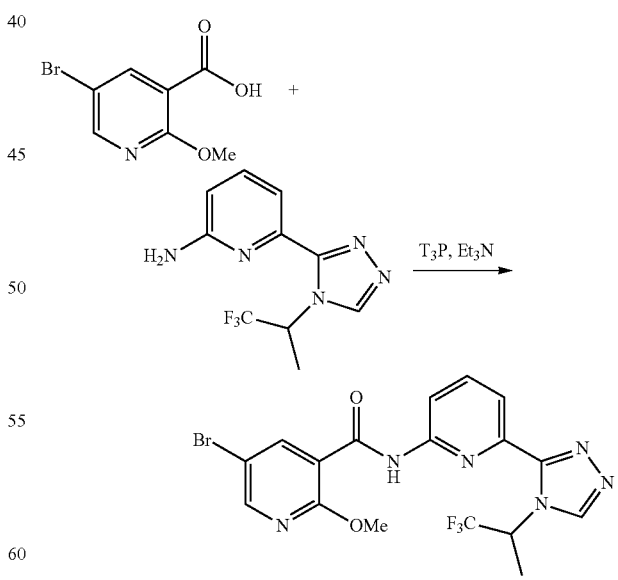

rac-5-Bromo-2-methoxy-N-(6-(4-(1,1,1-trifluoropropan-2-yl)-4H-1,2,4-triazol-3-yl)pyridin-2-yl)nicotinamide was prepared in an identical manner to that described for (S)-5-bromo-2-methoxy-N-(6-(4-(1,1,1-trifluoropropan-2-yl)-4H-1,2,4-triazol-3-yl)pyridin-2-yl)nicotinamide except rac-6-

[4-[2,2,2-trifluoro-1-methyl-ethyl]-1,2,4-triazol-3-yl]pyridin-2-amine (180 mg) was used instead of the (S) isomer. Filtration of the resulting solid afforded the desired compound as a tan solid (160 mg, 48%). $^1$H NMR (400 MHz, CD$_3$OD) δ 9.04 (s, 1H), 8.46-8.50 (m, 2H), 8.42 (dd, J=1.38, 7.91 Hz, 1H), 8.01-8.10 (m, 2H), 6.94 (quin, J=7.28 Hz, 1H), 4.17 (s, 3H), 1.90 (d, J=7.28 Hz, 3H). MS (ESI): 471.0 [(M+H) ($^{79}$Br)]$^+$.

Example 10: (R)-5-Bromo-2-methoxy-N-(6-(4-(1,1,1-trifluoropropan-2-yl)-4H-1,2,4-triazol-3-yl)pyridin-2-yl)nicotinamide

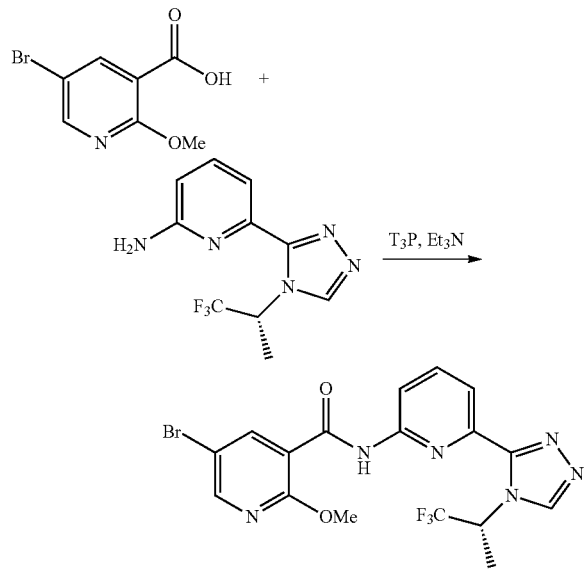

(R)-5-Bromo-2-methoxy-N-(6-(4-(1,1,1-trifluoropropan-2-yl)-4H-1,2,4-triazol-3-yl)pyridin-2-yl)nicotinamide was made in an identical manner to that described for (S)-5-bromo-2-methoxy-N-(6-(4-(1,1,1-trifluoropropan-2-yl)-4H-1,2,4-triazol-3-yl)pyridin-2-yl)nicotinamide except (R)-6-[4-[2,2,2-trifluoro-1-methyl-ethyl]-1,2,4-triazol-3-yl]pyridin-2-amine (180 mg) was used instead of the (S) isomer. Filtration of the resulting solid afforded the desired compound as a tan solid (130 mg, 39%). $^1$H NMR (400 MHz, CD$_3$OD) δ 9.01 (s, 1H), 8.45 (br d, J=5.52 Hz, 2H), 8.38 (br d, J=7.78 Hz, 1H), 7.95-8.09 (m, 2H), 6.91 (td, J=7.34, 14.43 Hz, 1H), 4.14 (s, 3H), 1.88 (d, J=7.03 Hz, 3H). MS (ESI): 471.0 [M+H ($^{79}$Br)]$^+$.

Example 11: (S)-2-Methoxy-5-methyl-N-(6-(4-(1,1,1-trifluoropropan-2-yl)-4H-1,2,4-triazol-3-yl)pyridin-2-yl)nicotinamide

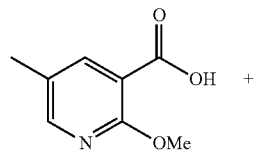

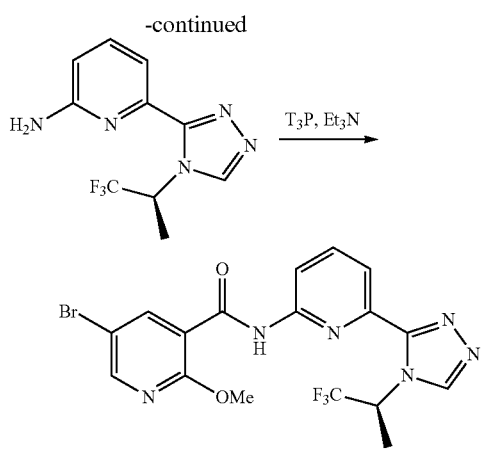

2-Methoxy-5-methyl-pyridine-3-carboxylic acid (88 mg, 0.52 mmol) and 6-[4-[(1S)-2,2,2-trifluoro-1-methyl-ethyl]-1,2,4-triazol-3-yl]pyridin-2-amine (135 mg, 0.52 mmol) were dissolved in triethylamine (0.73 mL, 5.25 mmol). Propylphosphonic anhydride (≥50 wt % in EtOAc, 0.55 mL) was added and the reaction was heated at 80° C. for 3 h. The reaction was cooled to rt and quenched by addition of MeOH (5 mL). The resulting solid was filtered and dried in vacuo to give the title compound (135 mg, 63%) as a white solid. $^1$H NMR (400 MHz, CDCl$_3$) δ 10.49 (s, 1H), 8.50 (dd, J=0.75, 8.28 Hz, 1H), 8.45 (d, J=1.00 Hz, 1H), 8.41-8.43 (m, 1H), 8.17 (dd, J=0.75, 2.51 Hz, 1H), 8.14 (dd, J=0.88, 7.66 Hz, 1H), 7.93 (t, J=8.03 Hz, 1H), 6.76 (quin, J=7.28 Hz, 1H), 4.17 (s, 3H), 2.37 (s, 3H), 1.83 (d, J=7.28 Hz, 3H). MS (ESI): 407.1 [M+H]$^+$.

Example 12: (S)-5-Fluoro-2-methoxy-N-(6-(4-(1,1,1-trifluoropropan-2-yl)-4H-1,2,4-triazol-3-yl)pyridin-2-yl)nicotinamide

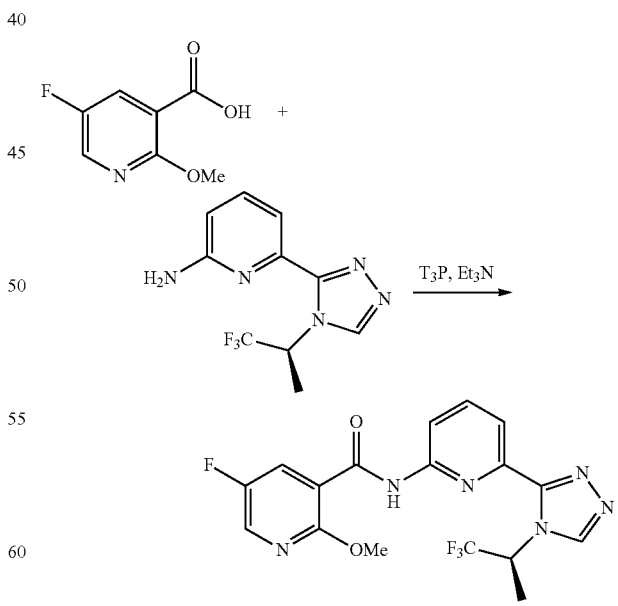

5-Fluoro-2-methoxy-pyridine-3-carboxylic acid (166 mg, 0.97 mmol) and 6-[4-[(1S)-2,2,2-trifluoro-1-methyl-ethyl]-1,2,4-triazol-3-yl]pyridin-2-amine (250 mg, 0.97 mmol) were dissolved in triethylamine (1.35 mL, 9.72 mmol) and propylphosphonic anhydride (≥50 wt % in EtOAc, 1.0 mL). The reaction was heated at 80° C. for 3 h. The reaction was cooled to rt, quenched by addition of MeOH (5 mL) and stirred for 1 h. The resulting solid was filtered and dried in vacuo to give the title compound (247 mg, 62%) as a white solid. ¹H NMR (400 MHz, CD₃OD) δ 9.02 (s, 1H), 8.38 (dd, J=1.63, 7.40 Hz, 1H), 8.27 (d, J=3.26 Hz, 1H), 8.14-8.21 (m, 1H), 7.97-8.04 (m, 2H), 6.89 (quin, J=7.22 Hz, 1H), 4.15 (s, 3H), 1.89 (d, J=7.28 Hz, 2H), 1.86-1.91 (m, 1H). MS (ESI): 411.1 [M+H]⁺.

Example 13: (S)-5-Chloro-2-methoxy-N-(6-(4-(1,1,1-trifluoropropan-2-yl)-4H-1,2,4-triazol-3-yl)pyridin-2-yl)nicotinamide

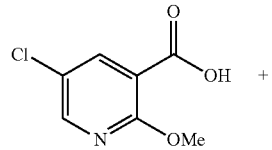

5-Chloro-2-methoxy-pyridine-3-carboxylic acid (182 mg, 0.97 mmol) and 6-[4-[(1S)-2,2,2-trifluoro-1-methyl-ethyl]-1,2,4-triazol-3-yl]pyridin-2-amine (250 mg, 0.97 mmol) were dissolved in triethylamine (1.35 mL, 9.72 mmol). Propylphosphonic anhydride (≥50 wt % in EtOAc, 1.0 mL) was added and the reaction was heated at 80° C. for 3 h. The reaction was cooled to rt, quenched by addition of MeOH (5 mL) and stirred for 1 h. The resulting solid was filtered and dried under vacuum to give the title compound (200 mg, 48%) as a white solid. ¹H NMR (400 MHz, CDCl₃) δ 10.37 (s, 1H), 8.58 (d, J=2.51 Hz, 1H), 8.43-8.49 (m, 2H), 8.31 (d, J=2.51 Hz, 1H), 8.16 (dd, J=0.75, 7.78 Hz, 1H), 7.95 (t, J=7.91 Hz, 1H), 6.71 (quin, J=7.22 Hz, 1H), 4.19 (s, 3H), 1.82 (d, J=7.28 Hz, 3H). MS (ESI): 427.0 [M+H]⁺.

Example 14: rac-N-(6-(4-(1,1-Difluoropropan-2-yl)-4H-1,2,4-triazol-3-yl)pyridin-2-yl)-2-methoxynicotinamide

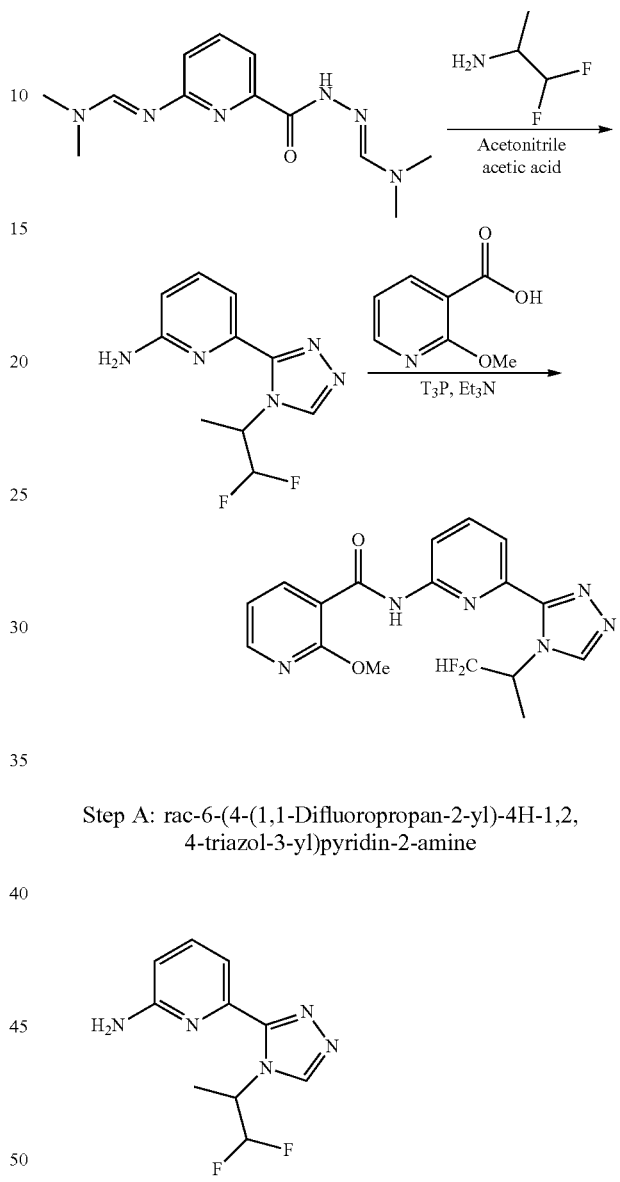

Step A: rac-6-(4-(1,1-Difluoropropan-2-yl)-4H-1,2,4-triazol-3-yl)pyridin-2-amine N,6-bis[(E)-Dimethylaminomethyleneamino]pyridine-2-carboxamide (600 mg, 2.29 mmol) and 1,1-difluoropropan-2-amine (435 mg, 3.31 mmol, hydrochloride salt) were dissolved in acetonitrile (6 mL) and acetic acid (2 mL). The reaction was heated in a sealed tube at 120° C. overnight. The reaction was cooled to rt and concentrated in vacuo. Purification by column chromatography using EtOAc as eluent gave the title compound (510 mg, 93%) as a white solid. ¹H NMR (400 MHz, CD₃OD) δ ppm 8.77 (s, 1H), 7.50-7.62 (m, 1H), 7.29 (dd, J=7.4, 0.9 Hz, 1H), 6.58-6.72 (m, 1H), 5.94-6.43 (m, 2H), 1.68 (d, J=7.3 Hz, 3H). MS (ESI): 240.1 [M+H]⁺.

Step B: rac-N-(6-(4-(1,1-Difluoropropan-2-yl)-4H-1,2,4-triazol-3-yl)pyridin-2-yl)-2-methoxynicotinamide

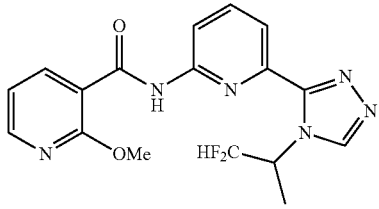

2-Methoxypyridine-3-carboxylic acid (64 mg, 0.42 mmol) and rac-6-[4-(2,2-difluoro-1-methyl-ethyl)-1,2,4-triazol-3-yl]pyridin-2-amine (100 mg, 0.42 mmol) were dissolved in triethylamine (0.58 mL, 4.18 mmol). Propylphosphonic anhydride (≥50 wt % in EtOAc, 0.43 mL) was added and the reaction was heated at 80° C. for 3 h. The reaction was cooled to rt and quenched by addition of MeOH (2 mL). The resulting solid was filtered and dried under vacuum to give the title compound (110 mg, 70%) as a tan solid. $^1$H NMR (400 MHz, CDCl$_3$) δ 10.39 (s, 1H), 8.61 (dd, J=2.01, 7.53 Hz, 1H), 8.53 (dd, J=0.75, 8.28 Hz, 1H), 8.41 (d, J=1.25 Hz, 1H), 8.38 (dd, J=2.01, 4.77 Hz, 1H), 8.10-8.16 (m, 1H), 7.94 (t, J=8.03 Hz, 1H), 7.12-7.19 (m, 1H), 6.13-6.45 (m, 1H), 5.86-6.04 (m, 1H), 4.21 (s, 3H), 1.75 (d, J=7.28 Hz, 3H). MS (ESI): 375.1 [M+H]$^+$.

Example 15: (S)—N-(6-(4-(1,1-Difluoropropan-2-yl)-4H-1,2,4-triazol-3-yl)pyridin-2-yl)-2-methoxynicotinamide and (R)—N-(6-(4-(1,1-Difluoropropan-2-yl)-4H-1,2,4-triazol-3-yl)pyridin-2-yl)-2-methoxynicotinamide

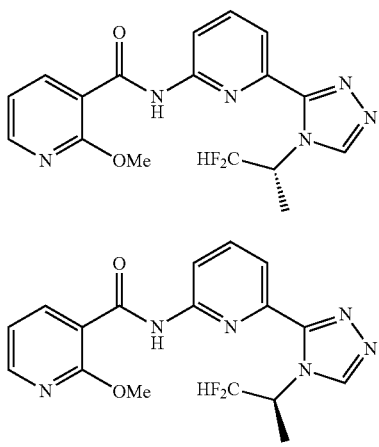

Chiral separation of N-[6-[4-(2,2-difluoro-1-methyl-ethyl)-1,2,4-triazol-3-yl]-2-pyridyl]-2-methoxy-pyridine-3-carboxamide (90 mg, 0.24 mmol) was performed by SFC (using a CHIRALPAK OX-H, 5 μm 30×250 mm column and using 40% MeOH (containing 0.1% Et$_2$NH) in CO$_2$ as the mobile phase and at a flow rate of 100 mL/min). The second eluting compound was assigned the (S) stereochemistry. $^1$H NMR (400 MHz, CDCl$_3$) δ 10.39 (s, 1H), 8.61 (dd, J=2.01, 7.53 Hz, 1H), 8.53 (dd, J=0.75, 8.28 Hz, 1H), 8.41 (d, J=1.25 Hz, 1H), 8.38 (dd, J=2.01, 4.77 Hz, 1H), 8.11-8.15 (m, 1H), 7.94 (t, J=8.03 Hz, 1H), 7.13-7.19 (m, 1H), 6.14-6.48 (m, 1H), 5.88-6.03 (m, 1H), 4.21 (s, 3H), 1.75 (d, J=7.28 Hz, 3H). MS (ESI): 375.1 [M+H]$^+$.

Example 16: 2-Methoxy-N-(6-(4-(1-(trifluoromethyl)cyclopropyl)-4H-1,2,4-triazol-3-yl)pyridin-2-yl)nicotinamide

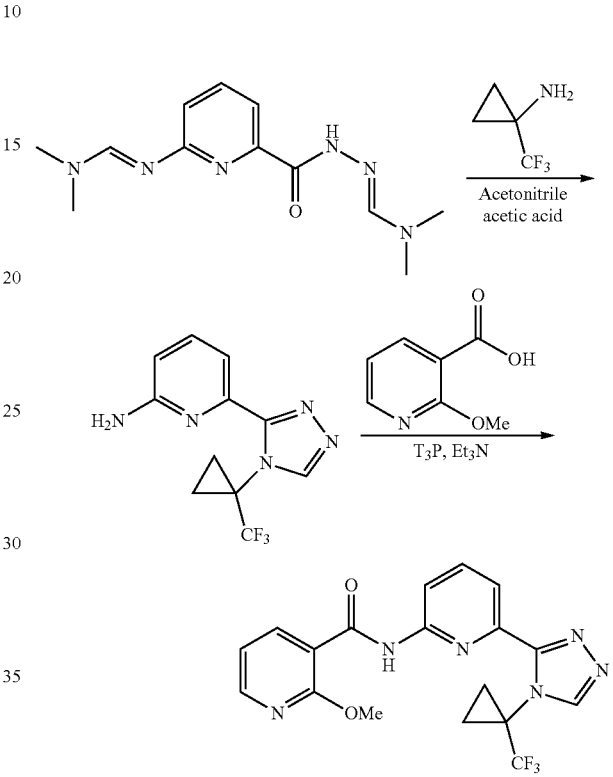

Step A: 6-(4-(1-(Trifluoromethyl)cyclopropyl)-4H-1,2,4-triazol-3-yl)pyridin-2-amine N,6-bis[(E)-Dimethylaminomethyleneamino]pyridine-2-carboxamide (1.00 g, 3.81 mmol) and 1-(trifluoromethyl)cyclopropanamine (950 mg, 7.62 mmol, 0.17 mL) were dissolved in a solution of acetonitrile (6 mL) and acetic acid (2 mL). The reaction was heated in a sealed tube at 120° C. overnight. The reaction was cooled to rt and the solvent was evaporated in vacuo. Purification by column chromatography using EtOAc as eluent gave the title compound (223 mg, 22%) as a white solid. MS (ESI): 270.1 [M+H]$^+$.

Step B: 2-Methoxy-N-(6-(4-(1-(trifluoromethyl)
cyclopropyl)-4H-1,2,4-triazol-3-yl)pyridin-2-yl)
nicotinamide

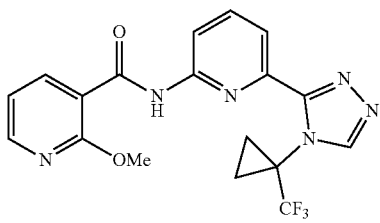 [SMILES: COc1ncccc1C(=O)Nc1cccc(-c2nncn2C2(C(F)(F)F)CC2)n1]

2-Methoxypyridine-3-carboxylic acid (57 mg, 0.37 mmol) and 6-[4-[1-(trifluoromethyl)cyclopropyl]-1,2,4-triazol-3-yl]pyridin-2-amine (100 mg, 0.37 mmol) were dissolved in triethylamine (0.52 mL, 3.71 mmol). Propylphosphonic anhydride (≥50 wt % in EtOAc, 0.38 mL) was added and the reaction was heated at 80° C. for 3 h. The reaction was cooled to rt and quenched by addition of MeOH (2 mL). The mixture was filtered and dried in vacuo to give the title compound (59 mg, 39%) as a white solid. ¹H NMR (400 MHz, CDCl₃) δ 10.41 (s, 1H), 8.63 (dd, J=2.01, 7.53 Hz, 1H), 8.54 (dd, J=1.00, 8.28 Hz, 1H), 8.40 (s, 1H), 8.37 (dd, J=2.01, 5.02 Hz, 1H), 8.05 (dd, J=0.88, 7.66 Hz, 1H), 7.88-7.93 (m, 1H), 7.16 (dd, J=4.77, 7.53 Hz, 1H), 4.20 (s, 3H), 1.75-1.83 (m, 2H), 1.46-1.56 (m, 2H). MS (ESI): 405.1 [M+H]⁺.

Example 17: 5-Fluoro-2-methoxy-N-(6-(4-(1-(trifluoromethyl)cyclopropyl)-4H-1,2,4-triazol-3-yl)pyridin-2-yl)nicotinamide

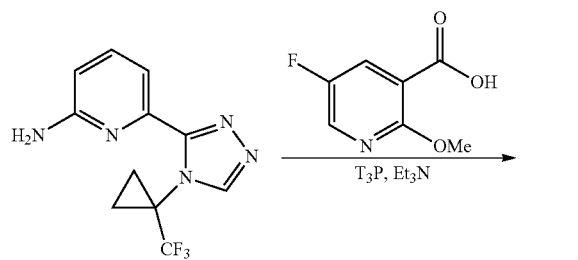

5-Fluoro-2-methoxy-N-(6-(4-(1-(trifluoromethyl)cyclopropyl)-4H-1,2,4-triazol-3-yl)pyridin-2-yl)nicotinamide was prepared in an identical manner as described for 2-methoxy-N-(6-(4-(1-(trifluoromethyl)cyclopropyl)-4H-1,2,4-triazol-3-yl)pyridin-2-yl)nicotinamide except 5-fluoro-2-methoxypyridine-3-carboxylic acid (63 mg) was used in place of 2-methoxypyridine-3-carboxylic acid. Filtration of the resulting solid gave the desired compound as a tan solid (120 mg, 76%). ¹H NMR (400 MHz, CDCl₃) δ 10.42 (br s, 1H), 8.52 (br d, J=8.28 Hz, 1H), 8.32-8.43 (m, 2H), 8.21 (br d, J=2.76 Hz, 1H), 8.06 (br d, J=7.78 Hz, 1H), 7.85-7.98 (m, 1H), 4.18 (s, 3H), 1.75-1.87 (m, 2H), 1.50 (br s, 2H). MS (ESI): 423.1 [M+H]⁺.

Example 18: rac-N-(6-(4-(2,2-Difluorocyclobutyl)-4H-1,2,4-triazol-3-yl)pyridin-2-yl)-2-methoxynicotinamide

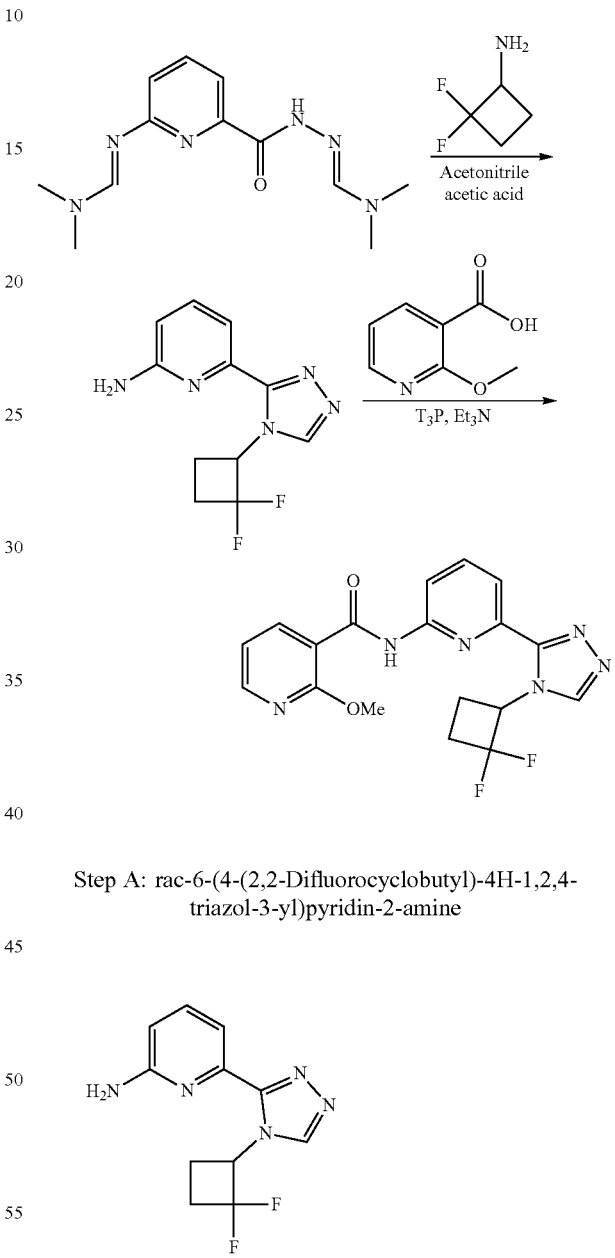

Step A: rac-6-(4-(2,2-Difluorocyclobutyl)-4H-1,2,4-triazol-3-yl)pyridin-2-amine

To a mixture of (E)-N'-(6-(2-((E)-(dimethylamino)methylene)hydrazine-1-carbonyl)pyridin-2-yl)-N,N-dimethylformimidamide (501 mg, 1.91 mmol) and 2,2-difluorocyclobutan-1-amine hydrochloride (558 mg, 3.89 mmol) was added acetonitrile (3 mL), and acetic acid (1 mL). The mixture was heated in a hot plate at 120° C. for 24 h. After this time the reaction was cooled to rt and partitioned between EtOAc and NaHCO₃ (saturated aqueous solution). The aqueous layer was extracted with EtOAc and the combined organic extracts were dried over MgSO₄, filtered and evaporated in vacuo. The residue was purified by column chromatography using EtOAc as eluent to give the title compound (203 mg, 42%). MS (ESI): 252.0 [M+H]⁺.

Step B: rac-N-(6-(4-(2,2-Difluorocyclobutyl)-4H-1,2,4-triazol-3-yl)pyridin-2-yl)-2-methoxynicotinamide

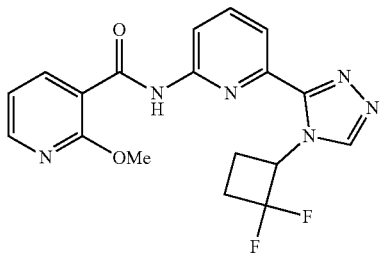 [SMILES: COc1ncccc1C(=O)Nc1cccc(-c2nncn2C2CCC2(F)F)n1]

To a mixture of rac-6-[4-(2,2-difluorocyclobutyl)-1,2,4-triazol-3-yl]pyridin-2-amine (50.0 mg, 0.20 mmol) and 2-methoxypyridine-3-carboxylic acid (33.5 mg, 0.22 mmol) in triethylamine (0.3 mL, 2.16 mmol) was added propylphosphonic anhydride (≥50 wt % in EtOAc, 0.5 mL). The mixture was heated in a microwave reactor at 110° C. for 1 h. After this time the reaction was quenched with a small amount of MeOH (~2 mL) and the mixture was partitioned between EtOAc and NaHCO₃ (saturated aqueous solution). The organic phase was separated and concentrated in vacuum. The product was purified by column chromatography using EtOAc/EtOH (7/1) as eluent to give the title compound (58 mg, yield 75%) as a white powder after lyophilization. ¹H NMR (400 MHz, CD₃OD) δ ppm 8.95 (d, J=2.01 Hz, 1H), 8.43-8.56 (m, 2H), 8.39 (dd, J=4.89, 1.88 Hz, 1H), 8.03 (t, J=8.03 Hz, 1H), 7.92 (d, J=7.28 Hz, 1H), 7.20 (dd, J=7.66, 4.89 Hz, 1H), 6.22-6.57 (m, 1H), 4.19 (s, 3H), 2.33-2.83 (m, 4H). MS (ESI): 387.1 [M+H]⁺.

Example 19 and 20: (R)—N-(6-(4-(2,2-Difluorocyclobutyl)-4H-1,2,4-triazol-3-yl)pyridin-2-yl)-2-methoxynicotinamide and (S)—N-(6-(4-(2,2-Difluorocyclobutyl)-4H-1,2,4-triazol-3-yl)pyridin-2-yl)-2-methoxynicotinamide

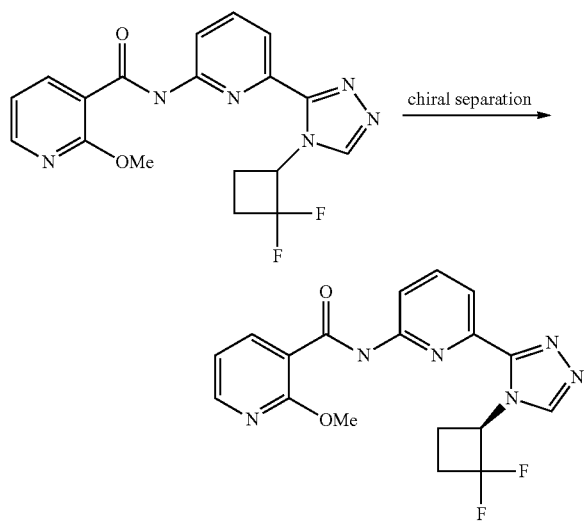

chiral separation

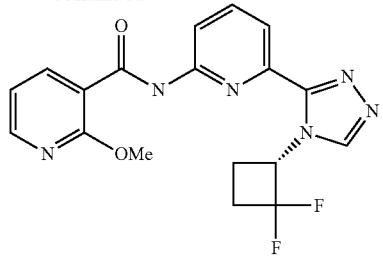

rac-N-(6-(4-(2,2-Difluorocyclobutyl)-4H-1,2,4-triazol-3-yl)pyridin-2-yl)-2-methoxynicotinamide (58 mg, 0.15 mmol, prepared from Example 18) was separated by chiral SFC (using a CHIRALPAK AD-H, 5 μm 30×250 mm column and using 25% MeOH (containing 0.1% Et₂NH) in CO₂ as the mobile phase at a flow rate of 100 mL/min) to give in order of elution:

Peak 1, (R)—N-(6-(4-(2,2-Difluorocyclobutyl)-4H-1,2,4-triazol-3-yl)pyridin-2-yl)-2-methoxynicotinamide, 9.8 mg (17%) (stereochemistry was arbitrarily assigned): ¹H NMR (400 MHz, CD₃OD) δ ppm 8.96 (d, J=1.76 Hz, 1H), 8.41-8.53 (m, 2H), 8.38 (dd, J=4.77, 2.01 Hz, 1H), 7.96-8.07 (m, 1H), 7.91 (d, J=7.28 Hz, 1H), 7.18 (dd, J=7.53, 4.77 Hz, 1H), 6.30-6.53 (m, 1H), 4.19 (s, 3H), 2.35-2.83 (m, 4H). 9.8 mg (17%). (ESI): 387.1 [M+H]⁺.

Peak 2, (S)—N-(6-(4-(2,2-Difluorocyclobutyl)-4H-1,2,4-triazol-3-yl)pyridin-2-yl)-2-methoxynicotinamide, 9.8 mg (17%) (stereochemistry was arbitrarily assigned): ¹H NMR (400 MHz, CD₃OD) δ ppm 8.97 (d, J=2.01 Hz, 1H), 8.48 (d, J=9.29 Hz, 2H), 8.39 (dd, J=4.77, 2.01 Hz, 1H), 7.96-8.09 (m, 1H), 7.92 (d, J=7.28 Hz, 1H), 7.19 (dd, J=7.53, 5.02 Hz, 1H), 6.20-6.68 (m, 1H), 4.20 (s, 3H), 2.45-2.91 (m, 4H). (ESI): 387.1 [M+H]⁺.

Example 21: Brief Description of ASK1 TR-FRET Assay

The protein kinase activity of 5 nM GST-hASK1 (Life Technologies PV4011) was assayed with 100 μM ATP and 2 μM of HTRF biotinylated STK Substrate 3 (CisBio Kit 62ST3PEJ), at ambient temperature in 25 mM Hepes, pH 7.5, 50 mM NaCl, 10 mM MgCl₂, 0.02% Brij-35, 1 mM DTT, and 1% DMSO.

Briefly, 20 μL aliquots of a 1.5× stock of ASK1, STK Substrate 3 and Assay Buffer were distributed in the wells of a white 384 well Optiplate, prior to addition of 0.3 μL of a 100× compound stock in DMSO, or DMSO alone in Blank and 100% Activity Controls. After a 10 minute pre-incubation, ASK1 protein kinase activity was initiated by addition of 10 μL of 300 μM ATP. After 5 hours, the kinase activity was quenched by addition of 30 μL of CisBio Kit 62ST3PEJ components: 0.5 μM of Streptavidin XL665; and 100×STK Antibody-Eu Cryptate; in Detection Buffer containing sufficient EDTA to chelate Mg²⁺ in the assay buffer. The plates were read after 65 minutes in an Envision Plate reader, with the following components and settings: Top Mirror, Lance Delfia Dual (662); UV Ex Filter, 320 nm (111); Emission Filter for donor, 615 nm (203); Emission Filter for Acceptor; 665 nm (205); and 100 μsec delay, with 665/615 ratio output.

After subtracting the blank from the control and test well values, the ASK1 dependent 665/615 ratio output was plotted versus log of compound concentration, and the IC$_{50}$ values obtained from a 4 parameter fit in Graphpad Prism.

Compound 1 has an IC$_{50}$ of less than 0.1 µM.

Alternatively, the protein kinase inhibitory activity of the compounds described herein were tested using the ASK1/MAP3K5 assay by Reaction Biology Corp. (Malvern, Pa.). The assay procedure follows (and is also available on the Reaction Biology Corp. website).

Base Reaction Buffer: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO;

Substrate: 20 µM of myelin basic protein (MBP) and 100 µM ATP;

Protein kinase: ASK1/MAP3K5.

Reaction Procedure:
1. Prepare indicated substrate in freshly prepared Base Reaction Buffer.
2. Deliver any required cofactors to the substrate solution.
3. Deliver indicated kinase into the substrate solution and gently mix.
4. Deliver compounds in DMSO into the kinase reaction mixture by Acoustic; technology (Echo550; nanoliter range), incubate for 20 minutes at room temperature.
5. Deliver $^{33}$P-ATP (specific activity 10 µCi/µL) into the reaction mixture to initiate the reaction.
6. Incubate kinase reaction for 2 hours at room temperature.
7. Reactions are spotted onto P81 ion exchange paper.
8. Detect kinase activity by filter-binding method.

The results are provided below, wherein the compound number corresponds to the numbers set forth in the examples above, "+" reprents an IC$_{50}$ of less than 10 µM, but greater than 1 µM, "++" represents an IC$_{50}$ of less than or equal to 1 µM but greater than 0.1 µM, and "+++" represents an IC$_{50}$ of less than or equal to 0.1 µM.

TABLE 1

| IC$_{50}$ | Compounds |
| --- | --- |
| +++ | 2, 3, 4, 5, 6, 8, 9, 11, 12, 13, 14, 15b, 16, 17, 18, 20 |
| ++ | 10, 15a, 19 |
| + | 7 |

Example 22: Brief Description of ASK1(AUTO PHOS T838) Assay

ASK1 T838 auto phosphorylation was measured in HEK-293T cells using MSD assay format. HEK 293T cells were seeded in 15 cm plates at a density of 18 million cells and 20 mL DMEM with 10% FBS, Pen/Strep media. The plates were incubated at 37° C. overnight. Media on plates was changed to OPTI-MEM, serum free media and cells were transfected with 9 µg of ASK1-V5 tagged full length plasmid using Lipofectamine 2000 (Invitrogen) and the plates were incubated at 37° C. overnight. Cells were trypsinized, counted on Nexcellometer and plated into 96 well tissue culture plates with 100,000 cells/well and 200 µL media. Cells were incubated for 4 hr at 37° C. then ASK1 compounds were added using a HP 300e. Compounds were tested at 20 µM with 3 fold, 10 point dilution points then incubated for 1 hr at 37° C. A lysis buffer (Cell Signaling) was prepared with protease and phosphatase inhibitor and maintained at 4° C. until use. Media from cells was discarded and 120 µL of cold lysis buffer was added to the cells, the plate was shaken 4° C. for 1 hr. Lysate was mixed using Apricot liquid handler; aspirating up and down 16 times at high speed using 50 µL volume. 50 µL of cell lysates were transferred to a pre-coated MSD plates containing mouse anti-V5 antibody (1:500 dilution) and washed 3× with MSD wash buffer (TBST) and blocked with a 3% BSA solution. Plates were then incubated on a plate shaker overnight at 4° C. Plates were washed 3× with MSD wash buffer and 50 µL of rabbit anti-pASK1 T838 antibody was added to the wells and incubated for 2 hr at room temperature on a plate shaker. Plates were then washed and 50 µL of goat anti-rabbit sulfa-tag (1:500 dilution) was added to wells, and incubated for 1 hr at room temperature on a plate shaker. Plates were washed 3× and 150 µL of 2×MSD Read buffer was added to wells. Plates were immediately read on a MSD Instrument Reader where chemoluminecense signal was measured. Data was analyzed using Graph Pad or Genedata, the data was normalized and plotted, % activity versus log of compound concentration. The IC$_{50}$ values were obtained from a 4 parameter fit.

The compounds described herein were tested for in the above cell-based assay. The results are provided in Table 3 below, wherein the compound number corresponds to the numbers set forth in the examples above, "†" represents an IC$_{50}$ of greater than 10 µM, "††" represents an IC$_{50}$ of equal to or less than 10 µM but greater than 1 µM, and "†††" represents an IC$_{50}$ of equal to or less than 1 µM.

TABLE 2

| IC$_{50}$ | Compounds |
| --- | --- |
| ††† | 1, 2, 3, 4, 5, 6, 7, 8, 9, 11, 12, 13, 14, 15b, 16, 18, 20 |
| †† | 10, 15a, 19 |
| † | 17 |

Example 23: Brief Description of MDR1-MDCK Assay

To predict the CNS penetration of the compounds described herein, several compounds were selected for an in vitro MDR1-MDCK assay. These experiments are conducted using human MDR1 transfected MDCK cells (Absorption Systems, Exton, Pa.) and the compounds are tested at 1 µM concentration prepared in transport buffer (Hank's balanced salt solution with HEPES) and following the steps below:
1. MDR1-MDCK cell are cultured for 7 days in 96 well transwell insert plates (Corning). Insert plates are washed before the assay and TEER (trans epithelial electric resistance) is measured.
2. These plates are loaded with test compound solution 85 µL for A-B transport and 260 µL for B-A transport in the respective donor compartment. The volume of receiver buffer (Transport buffer supplemented with 1% BSA) in the respective receiver compartment is 250 µL and 75 µL.
3. 10 µL samples is taken from donor compartment (T=0 timepoint)
4. Assay plates are incubated for 120 minutes.
5. At 120 minutes (T=120 timepoint) samples from respective donor (10 µL) and receiver (50 µL) compartments is taken.

6. After addition of 40 μL transport buffer with BSA to donor samples, crash solution (Acetonitrile with internal standard, 110 μL) is added to all samples.
7. After centrifugation 50 μL supernatant is transferred to separate plate and mixed with 50 μL water.
8. Samples are analyzed using LC-MS/MS coupled with high throughput injection system.
9. Analyte/internal standard area ratios are used for apparent permeability ($P_{app}$) and efflux ratio (ER) estimation based on equation below.

$$P_{app}=(dC_r/dt) \times V_r/(A \times C_E)$$

$$\text{Mass balance}=100 \times ((V_r \times C_r^{final})+(V_d \times C_d^{final}))/(V_d \times C_E)$$

Wherein:
$dC_r/dt$ is the cumulative concentration in the receiver compartment versus time in μM s$^{-1}$
$V_r$ is the volume of the receiver compartment in cm$^3$
$V_d$ is the volume of the donor compartment in cm$^3$
A is the area of the insert (0.143 cm$^2$ for 96-well insert)
$C_E$ is the estimated experimental concentration (Time=0) of the dosing solution
$C_r^{final}$ is the concentration of the receiver at the end of the incubation period
$C_d^{final}$ is the concentration of the donor at the end of the incubation period.

Each of the compounds described in examples 6, 12 and 16 was found to have an in vitro ER<3, which has been reported to correlate with good brain penetration (see Kikuchi, R. et al., *In vitro P-glycoprotein Efflux Ratio Can Predict the In Vivo Brain Penetration Regardless of Biopharmaceutics Drug Disposition Classification System Class.* Drug Metab Dispos 41:2012-2017, December 2013).

Example 24: In Vivo Brain Penetration

To evaluate the CNS penetration of the compounds described herein, several compounds were selected for in vivo rat $K_{puu}$ studies. In these experiments the compounds are administered via an IV infusion (using N,N-dimethylacetamide:ethanol:1,2-propylene glycol:water in a 1:1:3:5 ratio as the vehicle) in the carotid artery for a period of four hours (1 mg/kg, 0.1 mg/mL) to reach steady state. After this time the plasma and brain concentration levels are quantified, and the values are adjusted by the measured protein binding in plasma and brain homogenate to calculate the $K_{puu}$ (see Di, L.; Kerns, E. H. *Blood-Brain Barrier in Drug Discovery* (Wiley)) according to the equation below.

$$K_{puu}=C_{u,b}/C_{u,p}$$

Wherein:
$C_{u,b}$=Unbound concentration in brain ($C \times f_{u,b}$). (C=concentration at steady state; $f_{u,b}$=fraction unbound in brain)
And in which: $C_{u,p}$=Unbound concentration in plasma ($C \times f_{u,p}$). (C=concentration at steady state; $f_{u,p}$=fraction unbound in plasma)

Plasma and brain protein binding values were generated via the Rapid Equilibrium Dialysis method. The compound of interest was incubated in K$_2$EDTA plasma and brain homogenate (homogenized 1:7 (w:v) in 1×PBS) purchased from BioIVT (Westbury, N.Y.), opposite a buffered compartment of 100 mM Potassium phosphate/150 mM Sodium chloride, pH 7.4, at 1 μM for 4 hr and 6 hr respectively. At the conclusion of incubation samples were taken from both matrix and buffered compartments, matrix-matched using blank buffer and matrix, extracted with acetonitrile, diluted with water, and analyzed utilizing an Agilent RapidFire 365 high-throughput LC coupled with MS/MS detection via an AB Sciex 5500. Free fractions ($f_u$) were then calculated by comparing internal standard/analyte peak-area ratios of matrix and buffered compartments. Cross-species brain protein binding was considered to be equivalent for the purposes of calculating free fraction (see Di, L., et al., (2011a) *Species Independence in Brain Tissue Binding Using Brain Homogenates*, Drug Metab Dispos 39:1270-1277).

Total drug concentration in plasma and brain tissue was measured via well-established bioanalytical extraction (protein precipitation) and detection methods (LC-MS/MS). Brain tissues were homogenized 1:4 (w:v) with 1×PBS in MP Biomedicals Lysing Matrix D tubes via an MP Biomedicals FastPrep-24™ homogenizer and were then extracted alongside plasma samples by matrix-matching with blank K$_2$EDTA plasma (purchased from BioIVT), followed by protein crash/extraction with acetonitrile, supernatant dry down under nitrogen, and reconstitution with an acidified aqueous/organic mixture before being measured against a calibration curve of the compound of interest prepared in plasma, matrix-matched with blank brain homogenate (generated with brains purchased from BioIVT), and similarly extracted. Reconstituted extracts were then analyzed via LC-MS/MS (AB Sciex 5500) utilizing a binary HPLC setup (Shimadzu LC-20ADvp) and reverse-phase chromatography gradient (ACE 3 C18-AR). Peak area ratios and a 1/x$^2$ regression fit were used to generate sample concentration values that, combined with plasma and brain protein binding values, were used to generate free drug concentration values and partitioning coefficient ($K_{puu}$).

This experiment is conducted with the compounds described in examples 6, 12 and 16, and the $K_{puu}$ values are provided below.

TABLE 3

| Example | Rat $K_{puu}$ |
|---|---|
| 6 | 0.70 |
| 12 | 0.46 |
| 16 | 0.41 |

Aspects of the present invention are additionally set forth in the enumerated embodiments below.
1. A compound of Formula (I):

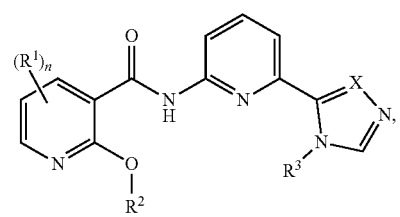

(I)

or a pharmaceutically acceptable salt thereof, wherein:
X is CR$^4$ or N;
n is 1 or 2;
R$^1$ in each occurrence is independently selected from H, C$_{1-6}$alkyl, C$_{2-6}$alkenyl, C$_{2-6}$alkynyl, halo, —CN, —C(O)R$^{1a}$, —C(O)OR$^{1a}$, —C(O)N(R$^{1a}$)$_2$, —N(R$^{1a}$)$_2$, —N(R$^{1a}$)C(O)R$^{1a}$, —N(R$^{1a}$)C(O)OR$^{1a}$, —N(R$^{1a}$)C(O)N(R$^{1a}$)$_2$, —N(R$^{1a}$)S(O)$_2$R$^{1a}$, —OR$^{1a}$, —OC(O)

R$^{1a}$, —OC(O)N(R$^{1a}$)$_2$, —SR$^{1a}$, —S(O)R$^{1a}$, —S(O)$_2$R$^{1a}$, —S(O)N(R$^{1a}$)$_2$, and —S(O)$_2$N(R$^{1a}$)$_2$, wherein said C$_{1-6}$alkyl, C$_{2-6}$alkenyl, and C$_{2-6}$alkynyl are optionally substituted with one or more R$^{10}$;

R$^{1a}$ in each occurrence is independently selected from H, C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl in each occurrence are optionally and independently substituted with one or more R$^{10}$;

R$^{10}$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{10a}$, —C(O)OR$^{10a}$, —C(O)N(R$^{10a}$)$_2$, —N(R$^{10a}$)$_2$, —N(R$^{10a}$)C(O)R$^{10a}$, —N(R$^{10a}$)C(O)OR$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$, wherein said C$_{1-6}$alkyl, C$_{2-6}$alkenyl, C$_{2-6}$alkynyl, carbocyclyl, and heterocyclyl in each occurrence are optionally and independently substituted with one or more substituents independently selected from halo, —CN, —C(O)R$^{10a}$, —C(O)OR$^{10a}$, —C(O)N(R$^{10a}$)$_2$, —N(R$^{10a}$)$_2$, —N(R$^{10a}$)C(O)R$^{10a}$, —N(R$^{10a}$)C(O)OR$^{10a}$, —N(R$^{10a}$)C(O)N(R$^{10a}$)$_2$, —N(R$^{10a}$)S(O)$_2$R$^{10a}$, —OR$^{10a}$, —OC(O)R$^{10a}$, —OC(O)N(R$^{10a}$)$_2$, —SR$^{10a}$, —S(O)R$^{10a}$, —S(O)$_2$R$^{10a}$, —S(O)N(R$^{10a}$)$_2$, and —S(O)$_2$N(R$^{10a}$)$_2$;

R$^{10a}$ in each occurrence is independently selected from H, C$_{1-6}$alkyl, C$_{2-6}$alkenyl, C$_{2-6}$alkynyl, carbocyclyl, and heterocyclyl;

R$^2$ is selected from H, C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl are optionally and independently substituted with one or more R$^{20}$;

R$^{20}$ in each occurrence is independently selected from C$_{1-6}$alkyl, halo and —OR$^{20a}$;

R$^{20a}$ is H or C$_{1-4}$alkyl;

R$^3$ is selected from H, C$_{1-6}$alkyl, C$_{2-6}$alkenyl, C$_{2-6}$alkynyl, carbocyclyl, and heterocyclyl, wherein said C$_{1-6}$alkyl, C$_{2-6}$alkenyl, C$_{2-6}$alkynyl, carbocyclyl, and heterocyclyl are optionally substituted with one or more R$^{30}$;

R$^{30}$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{30a}$, —C(O)OR$^{30a}$, —C(O)N(R$^{30a}$)$_2$, —N(R$^{30a}$)$_2$, —N(R$^{30a}$)C(O)R$^{30a}$, —N(R$^{30a}$)C(O)OR$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$, wherein said C$_{1-6}$alkyl, C$_{2-6}$alkenyl, C$_{2-6}$alkynyl, carbocyclyl, and heterocyclyl in each occurrence are optionally and independently substituted with one or more substituents independently selected from halo, —CN, —C(O)R$^{30a}$, —C(O)OR$^{30a}$, —C(O)N(R$^{30a}$)$_2$, —N(R$^{30a}$)$_2$, —N(R$^{30a}$)C(O)R$^{30a}$, —N(R$^{30a}$)C(O)OR$^{30a}$, —N(R$^{30a}$)C(O)N(R$^{30a}$)$_2$, —N(R$^{30a}$)S(O)$_2$R$^{30a}$, —OR$^{30a}$, —OC(O)R$^{30a}$, —OC(O)N(R$^{30a}$)$_2$, —SR$^{30a}$, —S(O)R$^{30a}$, —S(O)$_2$R$^{30a}$, —S(O)N(R$^{30a}$)$_2$, and —S(O)$_2$N(R$^{30a}$)$_2$;

R$^{30a}$ in each occurrence is independently selected from H, C$_{1-6}$alkyl, C$_{2-6}$alkenyl, C$_{2-6}$alkynyl, carbocyclyl, and heterocyclyl, wherein said carbocyclyl, and heterocyclyl are each optionally substituted with with one or more substituents independently selected from C$_{1-4}$alkyl and halo;

R$^4$ is selected from H, C$_{1-6}$alkyl, C$_{2-6}$alkenyl, C$_{2-6}$alkynyl, carbocyclyl, heterocyclyl, halo, —CN, —C(O)R$^{4a}$, —C(O)OR$^{4a}$, —C(O)N(R$^{4a}$)$_2$, —N(R$^{4a}$)$_2$, —N(R$^{4a}$)C(O)R$^{4a}$, —N(R$^{4a}$)C(O)OR$^{4a}$, —N(R$^{4a}$)C(O)N(R$^{4a}$)$_2$, —N(R$^{4a}$)S(O)$_2$R$^{4a}$, —OR$^{4a}$, —OC(O)R$^{4a}$, —OC(O)N(R$^{4a}$)$_2$, —SR$^{4a}$, —S(O)R$^{4a}$, —S(O)$_2$R$^{4a}$, —S(O)N(R$^{4a}$)$_2$, and —S(O)$_2$N(R$^{4a}$)$_2$, wherein said C$_{1-6}$alkyl, C$_{2-6}$alkenyl, C$_{2-6}$alkynyl, carbocyclyl, and heterocyclyl, are optionally substituted with one or more R$^{40}$;

R$^{40}$ in each occurrence is independently selected from C$_{1-6}$alkyl, C$_{2-6}$alkenyl, C$_{2-6}$alkynyl, carbocyclyl, heterocyclyl, halo, —CN, —C(O)R$^{40a}$, —C(O)OR$^{40a}$, —C(O)N(R$^{40a}$)$_2$, —N(R$^{40a}$)$_2$, —N(R$^{40a}$)C(O)R$^{40a}$, —N(R$^{40a}$)C(O)OR$^{40a}$, —N(R$^{40a}$)C(O)N(R$^{40a}$)$_2$, —N(R$^{40a}$)S(O)$_2$R$^{40a}$, —OR$^{40a}$, —OC(O)R$^{40a}$, —OC(O)N(R$^{40a}$)$_2$, —SR$^{40a}$, —S(O)R$^{40a}$, —S(O)$_2$R$^{40a}$, —S(O)N(R$^{40a}$)$_2$, and —S(O)$_2$N(R$^{40a}$)$_2$, wherein said C$_{1-6}$alkyl, C$_{2-6}$alkenyl, C$_{2-6}$alkynyl, carbocyclyl, and heterocyclyl in each occurrence are optionally and independently substituted with one or more substituents independently selected from halo, —CN, —C(O)R$^{40a}$, —C(O)OR$^{40a}$, —C(O)N(R$^{40a}$)$_2$, —N(R$^{40a}$)$_2$, —N(R$^{40a}$)C(O)R$^{40a}$, —N(R$^{40a}$)C(O)OR$^{40a}$, —N(R$^{40a}$)C(O)N(R$^{40a}$)$_2$, —N(R$^{40a}$)S(O)$_2$R$^{40a}$, —OR$^{40a}$, —OC(O)R$^{40a}$, —OC(O)N(R$^{40a}$)$_2$, —SR$^{40a}$, —S(O)R$^{40a}$, —S(O)$_2$R$^{40a}$, —S(O)N(R$^{40a}$)$_2$, and —S(O)$_2$N(R$^{40a}$)$_2$; and R$^{40a}$ in each occurrence is independently selected from H and C$_{1-4}$alkyl.

2. The compound of embodiment 1, wherein the compound is represented by Formula (II):

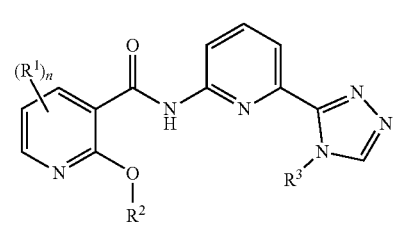

(II)

or a pharmaceutically acceptable salt thereof.

3. The compound of embodiment 1 or 2, wherein R$^2$ is C$_{1-6}$alkyl.

4. The compound of embodiment 1 or 2, wherein R$^2$ is —CH$_3$.

5. The compound of any one of embodiments 1-4, wherein n is 1.

6. The compound of any one of embodiments 1-5, wherein the compound is represented by formula (III):

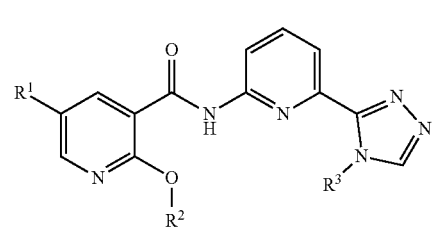

(III)

or a pharmaceutically acceptable salt thereof.

7. The compound of any one of embodiments 1-6, wherein:
$R^1$ in each occurrence is independently selected from H, $C_{1-6}$alkyl, $C_{2-6}$alkenyl, $C_{2-6}$alkynyl, halo, —CN, —C(O)$R^{1a}$, —C(O)O$R^{1a}$, —C(O)N($R^{1a}$)$_2$, —N($R^{1a}$)$_2$, —O$R^{1a}$, —S(O)$_2R^{1a}$, and —S(O)$_2$N($R^{1a}$)$_2$, wherein said $C_{1-6}$alkyl, $C_{2-6}$alkenyl, and $C_{2-6}$alkynyl are optionally substituted with one to four $R^{10}$;
$R^{1a}$ in each occurrence is independently selected from H, $C_{1-6}$alkyl, and 4- to 7-membered monocyclic N-containing non-aromatic heterocyclyl, wherein said $C_{1-6}$alkyl, and 4- to 7-membered monocyclic N-containing non-aromatic heterocyclyl in each occurrence are optionally and independently substituted with one to three $R^{10}$; and
$R^{10}$ in each occurrence is independently selected from $C_{1-6}$alkyl, halo, —N($R^{10a}$)$_2$, —O$R^{10a}$, —N($R^{10a}$)C(O)$R^{10a}$, —C(O)N($R^{10a}$)$_2$, —S$R^{10a}$, —S(O)$_2R^{10a}$, —S(O)$_2$N($R^{10a}$)$_2$, —CN, $C_{3-6}$cycloalkyl, and 4- to 7-membered monocyclic non-aromatic heterocyclyl, wherein said $C_{1-6}$alkyl, $C_{3-6}$cycloalkyl, and 4- to 7-membered monocyclic non-aromatic heterocyclyl are optionally substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$; and
$R^{10a}$ in each occurrence is independently H, $C_{1-4}$alkyl, halo$C_{1-4}$alkyl or $C_{3-6}$cycloalkyl.

8. The compound of any one of embodiments 1-6, wherein:
$R^1$ in each occurrence is independently selected from H, $C_{1-6}$alkyl and halo, wherein said $C_{1-6}$alkyl is optionally substituted with one to three $R^{10}$; and
$R^{10}$ in each occurrence is independently selected from $C_{1-6}$alkyl, halo, halo$C_{1-6}$alkyl and $C_{3-6}$cycloalkyl.

9. The compound of any one of embodiments 1-6, wherein:
n is 1;
$R^1$ is selected from H, —F, —Cl, —Br, —CF$_3$, or —CH$_3$.

10. The compound of any one of embodiments 1-9, wherein:
$R^3$ is selected from $C_{1-6}$alkyl, $C_{2-6}$alkynyl, $C_{3-6}$cycloalkyl and 5- to 6-membered N-containing heteroaryl, wherein said $C_{1-6}$alkyl, $C_{2-6}$alkynyl, $C_{3-6}$cycloalkyl and 5- to 6-membered N-containing heteroaryl are optionally substituted with one or three $R^{30}$;
$R^{30}$ in each occurrence is independently selected from $C_{1-6}$alkyl, phenyl, $C_{3-6}$cycloalkyl, 5- to 6-membered N-containing heteroaryl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —O$R^{30a}$, and —OC(O)$R^{30a}$, wherein said $C_{1-6}$alkyl, phenyl, $C_{3-6}$cycloalkyl, and 5- to 6-membered N-containing heteroaryl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, phenyl, and 5- to 6-membered N-containing heteroaryl, wherein said $C_{1-6}$alkyl, phenyl, and 5- to 6-membered N-containing heteroaryl is optionally substituted with one to three substituents independently selected from $C_{1-4}$alkyl and halo.

11. The compound of any one of embodiments 1-9, wherein:
$R^3$ is $C_{1-6}$alkyl or $C_{3-6}$cycloalkyl, wherein said $C_{1-6}$alkyl and $C_{3-6}$cycloalkyl are each optionally substituted with one to three $R^{30}$;
$R^{30}$ in each occurrence is independently $C_{1-6}$alkyl or halo, wherein said $C_{1-6}$alkyl is optionally substituted with one to three halo.

12. The compound of any one of embodiments 1-9, wherein:
$R^3$ is —CH(CH$_3$)CF$_3$, —CH(CH$_3$)CHF$_2$, —CH(CH$_3$)$_2$, —CH(CH$_3$)CH(CH$_3$)$_2$, cyclopropyl, or cyclobutyl, wherein said cyclopropyl and cyclobutyl are optionally substituted with one or two fluoro or —CF$_3$.

13. The compound of embodiment 1, wherein the compound is represented by formula (IV):

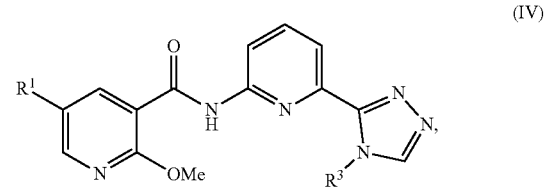

or a pharmaceutically acceptable salt thereof, wherein:
$R^1$ is H, halo, or $C_{1-6}$alkyl; and
$R^3$ is $C_{1-6}$alkyl or $C_{3-6}$cycloalkyl, wherein said $C_{1-6}$alkyl and $C_{3-6}$cycloalkyl are optionally substituted with one to three fluoro, $C_{1-4}$alkyl or halo$C_{1-4}$alkyl.

14. The compound of embodiment 13, wherein $R^3$ is $C_{1-3}$alkyl, cyclopropyl or cyclobutyl, wherein said $C_{1-3}$alkyl, cyclopropyl and cyclobutyl are optionally substituted with one or two substituents independently selected from fluoro, $C_{1-3}$alkyl and halo$C_{1-3}$alkyl.

15. The compound of embodiment 13, wherein:
$R^1$ is H, —F, —Cl, —Br, or —CH$_3$; and
$R^3$ is —CH(CF$_3$)CH$_3$, —CH(CHF$_2$)CH$_3$, or —CH(CH$_2$F)CH$_3$.

16. The compound of embodiment 13, wherein:
$R^1$ is H, —F, —Cl, —Br, or —CH$_3$; and
$R^3$ is cyclopropyl or cyclobutyl, wherein said cyclopropyl and cyclobutyl are optionally substituted with one or two substituents independently selected from fluoro and —CF$_3$.

17. The compound of embodiment 13, wherein:
$R^1$ is H, —F, —Cl, —Br, or —CH$_3$; and
$R^3$ is

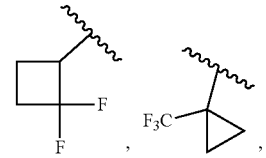

—CH(CF$_3$)CH$_3$, or —CH(CH$_3$)$_2$.

18. The compound of embodiment 17, wherein:
R³ is

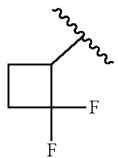

19. The compound of embodiment 17, wherein:
R³ is

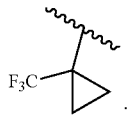

20. The compound of embodiment 17, wherein R³ is —CH(CF₃)CH₃.
21. The compound of embodiment 17, wherein R³ is —CH(CH₃)CH₃.
22. The compound of embodiment 1, wherein the compound is:
N-(6-(4-isopropyl-4H-1,2,4-triazol-3-yl)pyridin-2-yl)-2-methoxynicotinamide;
2-hydroxy-N-(6-(4-isopropyl-4H-1,2,4-triazol-3-yl)pyridin-2-yl)nicotinamide;
N-(6-(4-cyclobutyl-4H-1,2,4-triazol-3-yl)pyridin-2-yl)-2-methoxynicotinamide;
5-bromo-2-methoxy-N-(6-(4-(1,1,1-trifluoropropan-2-yl)-4H-1,2,4-triazol-3-yl)pyridin-2-yl)nicotinamide;
N-(6-(4-(1,1-difluoropropan-2-yl)-4H-1,2,4-triazol-3-yl)pyridin-2-yl)-2-methoxynicotinamide;
2-methoxy-N-(6-(4-(1-(trifluoromethyl)cyclopropyl)-4H-1,2,4-triazol-3-yl)pyridin-2-yl)nicotinamide;
5-fluoro-2-methoxy-N-(6-(4-(1-(trifluoromethyl)cyclopropyl)-4H-1,2,4-triazol-3-yl)pyridin-2-yl)nicotinamide; or
N-(6-(4-(2,2-difluorocyclobutyl)-4H-1,2,4-triazol-3-yl)pyridin-2-yl)-2-methoxynicotinamide;
or a pharmaceutically acceptable salt thereof.
23. The compound of embodiment 1, wherein the compound is:
(S)-2-methoxy-N-(6-(4-(1,1,1-trifluoropropan-2-yl)-4H-1,2,4-triazol-3-yl)pyridin-2-yl)nicotinamide;
(S)-5-bromo-2-methoxy-N-(6-(4-(1,1,1-trifluoropropan-2-yl)-4H-1,2,4-triazol-3-yl)pyridin-2-yl)nicotinamide;
(S)-2-methoxy-5-methyl-N-(6-(4-(1,1,1-trifluoropropan-2-yl)-4H-1,2,4-triazol-3-yl)pyridin-2-yl)nicotinamide;
(S)-5-fluoro-2-methoxy-N-(6-(4-(1,1,1-trifluoropropan-2-yl)-4H-1,2,4-triazol-3-yl)pyridin-2-yl)nicotinamide; or
(S)-5-chloro-2-methoxy-N-(6-(4-(1,1,1-trifluoropropan-2-yl)-4H-1,2,4-triazol-3-yl)pyridin-2-yl)nicotinamide;
or a pharmaceutically acceptable salt thereof.
24. The compound of embodiment 1, wherein the compound is:
(R)-2-methoxy-N-(6-(4-(1,1,1-trifluoropropan-2-yl)-4H-1,2,4-triazol-3-yl)pyridin-2-yl)nicotinamide; or
(R)-5-bromo-2-methoxy-N-(6-(4-(1,1,1-trifluoropropan-2-yl)-4H-1,2,4-triazol-3-yl)pyridin-2-yl)nicotinamide;
or a pharmaceutically acceptable salt thereof.
25. A pharmaceutical composition comprising a compound of any one of embodiments 1-24 or a pharmaceutically acceptable salt thereof, and a pharmaceutically acceptable excipient.

26. A method for treating a disorder responsive to inhibition of apoptosis signal-regulating kinase 1 (ASK1) in a subject comprising administering to the subject an effective amount of a compound of any one of embodiments 1-24, or a pharmaceutically acceptable salt thereof.
27. The method of embodiment 26, wherein the disorder is neurodegenerative disorder, cardiovascular disease, metabolic disorder, inflammatory disease, autoimmune disorder, destructive bone disorder, polyglutamine disease, glutamate neurotoxicity, pain, traumatic brain injury, hemorrhagic stroke, ischemia, acute hypoxia, kidney fibrosis (renal fibrosis), kidney injury, diabetic kidney disease, diabetic nephropathy, non-alcoholic steatohepatitis (NASH), pulmonary arterial hypertension (PAH), optic neuritis, liver disease, respiratory disease, heart reperfusion injury, cardiac hypertrophy, cardiac fibrosis, energy metabolic disorder, cancer or infection.
28. A method for treating a neurodegenerative disorder in a subject comprising administering to the subject an effective amount of a compound of any one of embodiments 1-24 or a pharmaceutically acceptable salt thereof.
29. The method of embodiment 28, wherein the neurodegenerative disorder is Alzheimer's disease (AD), Parkinson's disease, Huntington's disease, or amyotrophic lateral sclerosis (ALS).
30. A method for treating an autoimmune disease in a subject comprising administering to the subject an effective amount of a compound of any one of embodiments 1-24 or a pharmaceutically acceptable salt thereof.
31. The method of embodiment 30, wherein the autoimmune disease is multiple sclerosis.
32. A method for treating a cardiovascular disease in a subject comprising administering to the subject an effective amount of a compound of any one of embodiments 1-24 or a pharmaceutically acceptable salt thereof.
33. The method of embodiment 32, wherein the cardiovascular disease is ischemia.
34. A method for treating stroke in a subject comprising administering to the subject an effective amount of a compound of any one of embodiments 1-24 or a pharmaceutically acceptable salt thereof.
35. A method for treating traumatic brain injury in a subject comprising administering to the subject an effective amount of a compound of any one of embodiments 1-24 or a pharmaceutically acceptable salt thereof.

What is claimed is:
1. A compound of Formula (I):

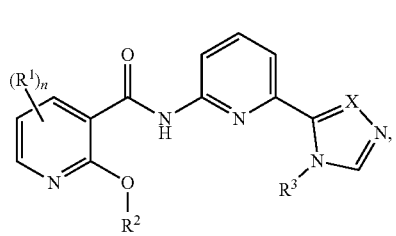

or a pharmaceutically acceptable salt thereof, wherein:
X is CR⁴ or N;

n is 1 or 2;

$R^1$ in each occurrence is independently selected from H, $C_{1-6}$alkyl, $C_{2-6}$alkenyl, $C_{2-6}$alkynyl, halo, —CN, —C(O)$R^{1a}$, —C(O)O$R^{1a}$, —C(O)N($R^{1a}$)$_2$, —N($R^{1a}$)$_2$, —N($R^{1a}$)C(O)$R^{1a}$, —N($R^{1a}$)C(O)O$R^{1a}$, —N($R^{1a}$)C(O)N($R^{1a}$)$_2$, —N($R^{1a}$)S(O)$_2$$R^{1a}$, —O$R^{1a}$, —OC(O)$R^{1a}$, —OC(O)N($R^{1a}$)$_2$, —S$R^{1a}$, —S(O)$R^{1a}$, —S(O)$_2$$R^{1a}$, —S(O)N($R^{1a}$)$_2$, and —S(O)$_2$N($R^{1a}$)$_2$, wherein said $C_{1-6}$alkyl, $C_{2-6}$alkenyl, and $C_{2-6}$alkynyl are optionally substituted with one or more $R^{10}$;

$R^{1a}$ in each occurrence is independently selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl in each occurrence are optionally and independently substituted with one or more $R^{10}$;

$R^{10}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2$$R^{10a}$, —O$R^{10a}$, —OC(O)$R^{10a}$, —OC(O)N($R^{10a}$)$_2$, —S$R^{10a}$, —S(O)$R^{10a}$, —S(O)$_2$$R^{10a}$, —S(O)N($R^{10a}$)$_2$, and —S(O)$_2$N($R^{10a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2$$R^{10a}$, —O$R^{10a}$, —OC(O)$R^{10a}$, —OC(O)N($R^{10a}$)$_2$, —S$R^{10a}$, —S(O)$R^{10a}$, —S(O)$_2$$R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, carbocyclyl, and heterocyclyl;

$R^2$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally and independently substituted with one or more $R^{20}$;

$R^{20}$ in each occurrence is independently selected from $C_{1-6}$alkyl, halo and —O$R^{20a}$;

$R^{20a}$ is H or $C_{1-4}$alkyl;

$R^3$ is selected from H, $C_{1-6}$alkyl, $C_{2-6}$alkenyl, $C_{2-6}$alkynyl, carbocyclyl, and heterocyclyl, wherein said $C_{1-6}$alkyl, $C_{2-6}$alkenyl, $C_{2-6}$alkynyl, carbocyclyl, and heterocyclyl are optionally substituted with one or more $R^{30}$;

$R^{30}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2$$R^{30a}$, —O$R^{30a}$, —OC(O)$R^{30a}$, —OC(O)N($R^{30a}$)$_2$, —S$R^{30a}$, —S(O)$R^{30a}$, —S(O)$_2$$R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, carbocyclyl, and heterocyclyl, wherein said carbocyclyl, and heterocyclyl are each optionally substituted with one or more substituents independently selected from $C_{1-4}$alkyl and halo;

$R^4$ is selected from H, $C_{1-6}$alkyl, $C_{2-6}$alkenyl, $C_{2-6}$alkynyl, carbocyclyl, heterocyclyl, halo, and —CN, wherein said $C_{1-6}$alkyl, $C_{2-6}$alkenyl, $C_{2-6}$alkynyl, carbocyclyl, and heterocyclyl, are optionally substituted with one or more $R^{40}$;

$R^{40}$ in each occurrence is independently selected from $C_{1-6}$alkyl, $C_{2-6}$alkenyl, $C_{2-6}$alkynyl, carbocyclyl, heterocyclyl, halo, —CN, —C(O)$R^{40a}$, —C(O)O$R^{40a}$, —C(O)N($R^{40a}$)$_2$, —N($R^{40a}$)$_2$, —N($R^{40a}$)C(O)$R^{40a}$, —N($R^{40a}$)C(O)O$R^{40a}$, —N($R^{40a}$)C(O)N($R^{40a}$)$_2$, —N($R^{40a}$)S(O)$_2$$R^{40a}$, —O$R^{40a}$, —OC(O)$R^{40a}$, —OC(O)N($R^{40a}$)$_2$, —S$R^{40a}$, —S(O)$R^{40a}$, —S(O)$_2$$R^{40a}$, —S(O)N($R^{40a}$)$_2$, and —S(O)$_2$N($R^{40a}$)$_2$, wherein said $C_{1-6}$alkyl, $C_{2-6}$alkenyl, $C_{2-6}$alkynyl, carbocyclyl, and heterocyclyl in each occurrence are optionally and independently substituted with one or more substituents independently selected from halo, —CN, —C(O)$R^{40a}$, —C(O)O$R^{40a}$, —C(O)N($R^{40a}$)$_2$, —N($R^{40a}$)$_2$, —N($R^{40a}$)C(O)$R^{40a}$, —N($R^{40a}$)C(O)O$R^{40a}$, —N($R^{40a}$)C(O)N($R^{40a}$)$_2$, —N($R^{40a}$)S(O)$_2$$R^{40a}$, —O$R^{40a}$, —OC(O)$R^{40a}$, —OC(O)N($R^{40a}$)$_2$, —S$R^{40a}$, —S(O)$R^{40a}$, —S(O)$_2$$R^{40a}$, —S(O)N($R^{40a}$)$_2$, and —S(O)$_2$N($R^{40a}$)$_2$; and $R^{40a}$ in each occurrence is independently selected from H and $C_{1-4}$alkyl.

2. The compound of claim 1, wherein the compound is represented by Formula (II):

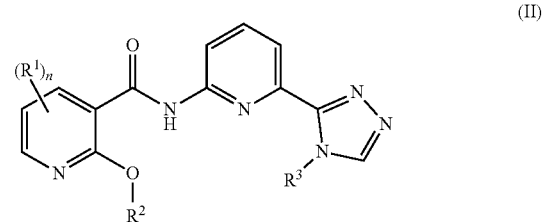

(II)

or a pharmaceutically acceptable salt thereof.

3. The compound of claim 2, wherein $R^2$ is $C_{1-6}$alkyl.

4. The compound of claim 3, wherein $R^2$ is —CH$_3$.

5. The compound of claim 2, wherein n is 1.

6. The compound of claim 1, wherein the compound is represented by formula (III):

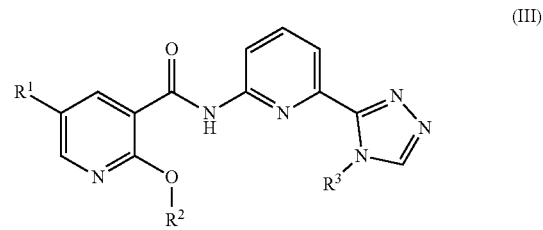

(III)

or a pharmaceutically acceptable salt thereof.

7. The compound of claim 6, wherein:

$R^1$ in each occurrence is independently selected from H, $C_{1-6}$alkyl, $C_{2-6}$alkenyl, $C_{2-6}$alkynyl, halo, —CN, —C(O)$R^{1a}$, —C(O)O$R^{1a}$, —C(O)N($R^{1a}$)$_2$, —N($R^{1a}$)$_2$, —O$R^{1a}$, —S(O)$_2R^{1a}$, and —S(O)$_2$N($R^{1a}$)$_2$, wherein said $C_{1-6}$alkyl, $C_{2-6}$alkenyl, and $C_{2-6}$alkynyl are optionally substituted with one to four $R^{10}$;

$R^{1a}$ in each occurrence is independently selected from H, $C_{1-6}$alkyl, and 4- to 7-membered monocyclic N-containing non-aromatic heterocyclyl, wherein said $C_{1-6}$alkyl, and 4- to 7-membered monocyclic N-containing non-aromatic heterocyclyl in each occurrence are optionally and independently substituted with one to three $R^{10}$; and $R^{10}$ in each occurrence is independently selected from $C_{1-6}$alkyl, halo, —N($R^{10a}$)$_2$, —O$R^{10a}$, —N($R^{10a}$)C(O)$R^{10a}$, —C(O)N($R^{10a}$)$_2$, —S$R^{10a}$, —S(O)$_2R^{10a}$, —S(O)$_2$N($R^{10a}$)$_2$, —CN, $C_{3-6}$cycloalkyl, and 4- to 7-membered monocyclic non-aromatic heterocyclyl, wherein said $C_{1-6}$alkyl, $C_{3-6}$cycloalkyl, and 4- to 7-membered monocyclic non-aromatic heterocyclyl are optionally substituted with one or more substituents independently selected from halo, —CN, —C(O)$R^{10a}$, —C(O)O$R^{10a}$, —C(O)N($R^{10a}$)$_2$, —N($R^{10a}$)$_2$, —N($R^{10a}$)C(O)$R^{10a}$, —N($R^{10a}$)C(O)O$R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently H, $C_{1-4}$alkyl, or $C_{3-6}$cycloalkyl; and $R^2$ is $C_{1-6}$alkyl.

8. The compound of claim 6, wherein:

$R^1$ in each occurrence is independently selected from H, $C_{1-6}$alkyl and halo, wherein said $C_{1-6}$alkyl is optionally substituted with one to three $R^{10}$;

$R^{10}$ in each occurrence is independently selected from $C_{1-6}$alkyl, halo, halo$C_{1-6}$alkyl and $C_{3-6}$cycloalkyl; and $R^2$ is $C_{1-6}$alkyl.

9. The compound of claim 6, wherein:

n is 1;

$R^1$ is selected from H, —F, —Cl, —Br, —CF$_3$, or —CH$_3$; and $R^2$ is $C_{1-6}$alkyl.

10. The compound of claim 7, wherein:

$R^3$ is selected from $C_{1-6}$alkyl, $C_{2-6}$alkynyl, $C_{3-6}$cycloalkyl and 5- to 6-membered N-containing heteroaryl, wherein said $C_{1-6}$alkyl, $C_{2-6}$alkynyl, $C_{3-6}$cycloalkyl and 5- to 6-membered N-containing heteroaryl are optionally substituted with one or three $R^{30}$;

$R^{30}$ in each occurrence is independently selected from $C_{1-6}$alkyl, phenyl, $C_{3-6}$cycloalkyl, 5- to 6-membered N-containing heteroaryl, halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —O$R^{30a}$, and —OC(O)$R^{30a}$, wherein said $C_{1-6}$alkyl, phenyl, $C_{3-6}$cycloalkyl, and 5- to 6-membered N-containing heteroaryl in each occurrence are optionally and independently substituted with one or more substituents independently selected from halo, —CN, —C(O)$R^{30a}$, —C(O)O$R^{30a}$, —C(O)N($R^{30a}$)$_2$, —N($R^{30a}$)$_2$, —N($R^{30a}$)C(O)$R^{30a}$, —N($R^{30a}$)C(O)O$R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, phenyl, and 5- to 6-membered N-containing heteroaryl, wherein said $C_{1-6}$alkyl, phenyl, and 5- to 6-membered N-containing heteroaryl is optionally substituted with one to three substituents independently selected from $C_{1-4}$alkyl and halo.

11. The compound of claim 7, wherein:

$R^3$ is $C_{1-6}$alkyl or $C_{3-6}$cycloalkyl, wherein said $C_{1-6}$alkyl and $C_{3-6}$cycloalkyl are each optionally substituted with one to three $R^{30}$;

$R^{30}$ in each occurrence is independently $C_{1-6}$alkyl or halo, wherein said $C_{1-6}$alkyl is optionally substituted with one to three halo.

12. The compound of claim 7, wherein:

$R^3$ is —CH(CH$_3$)CF$_3$, —CH(CH$_3$)CHF$_2$, —CH(CH$_3$)$_2$, —CH(CH$_3$)CH(CH$_3$)$_2$, cyclopropyl, or cyclobutyl, wherein said cyclopropyl and cyclobutyl are optionally substituted with one or two fluoro or —CF$_3$.

13. The compound of claim 1, wherein the compound is represented by formula (IV):

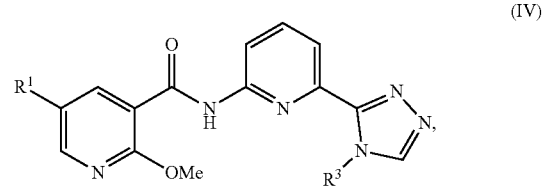

(IV)

or a pharmaceutically acceptable salt thereof, wherein:

$R^1$ is H, halo, or $C_{1-6}$alkyl; and $R^3$ is $C_{1-6}$alkyl or $C_{3-6}$cycloalkyl, wherein said $C_{1-6}$alkyl and $C_{3-6}$cycloalkyl are optionally substituted with one to three fluoro, $C_{1-4}$alkyl or halo$C_{1-4}$alkyl.

14. The compound of claim 13, wherein $R^3$ is $C_{1-3}$alkyl, cyclopropyl or cyclobutyl, wherein said $C_{1-3}$alkyl, cyclopropyl and cyclobutyl are optionally substituted with one or two substituents independently selected from fluoro, $C_{1-3}$alkyl and halo$C_{1-3}$alkyl.

15. The compound of claim 13, wherein:

$R^1$ is H, —F, —Cl, —Br, or —CH$_3$; and $R^3$ is

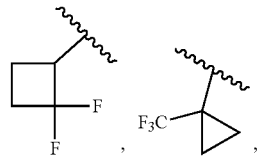 [SMILES: *C1CCC1(F)F ; *C1(C(F)(F)F)CC1]

—CH(CF$_3$)CH$_3$, or —CH(CH$_3$)$_2$.

16. A pharmaceutical composition comprising a compound of claim 1 or a pharmaceutically acceptable salt thereof, and a pharmaceutically acceptable excipient.

* * * * *

UNITED STATES PATENT AND TRADEMARK OFFICE
CERTIFICATE OF CORRECTION

| | |
|---|---|
| PATENT NO. | : 11,814,362 B2 |
| APPLICATION NO. | : 17/253269 |
| DATED | : November 14, 2023 |
| INVENTOR(S) | : Felix Gonzalez Lopez de Turiso et al. |

It is certified that error appears in the above-identified patent and that said Letters Patent is hereby corrected as shown below:

In the Claims

In Claim 1:
At the Column 47, Line number 7, replace "–$OR^{1la}$" with -- –$OR^{1a}$ --.

Signed and Sealed this
Eleventh Day of June, 2024

Katherine Kelly Vidal
*Director of the United States Patent and Trademark Office*